(12) United States Patent
Chomas et al.

(10) Patent No.: US 11,850,398 B2
(45) Date of Patent: Dec. 26, 2023

(54) SYSTEMS AND METHODS FOR PRESSURE-FACILITATED THERAPEUTIC AGENT DELIVERY

(71) Applicant: TriSalus Life Sciences, Inc., Westminster, CO (US)

(72) Inventors: James E. Chomas, Denver, CO (US); Aravind Arepally, Atlanta, GA (US); David Benjamin Jaroch, Arvada, CO (US); Mike Bojanowski, Denver, CO (US)

(73) Assignee: TriSalus Life Sciences, Inc., Westminster, CO (US)

( * ) Notice: Subject to any disclaimer, the term of this patent is extended or adjusted under 35 U.S.C. 154(b) by 367 days.

(21) Appl. No.: 16/408,266

(22) Filed: May 9, 2019

(65) Prior Publication Data
US 2020/0038586 A1 Feb. 6, 2020

Related U.S. Application Data

(60) Provisional application No. 62/713,410, filed on Aug. 1, 2018.

(51) Int. Cl.
*A61M 5/172* (2006.01)
*A61M 5/00* (2006.01)
(Continued)

(52) U.S. Cl.
CPC .......... *A61M 5/1723* (2013.01); *A61M 5/007* (2013.01); *A61M 5/16877* (2013.01);
(Continued)

(58) Field of Classification Search
CPC .......... A61B 17/1204; A61B 17/12109; A61B 17/12136; A61B 17/12168; A61B 5/0275;
(Continued)

(56) References Cited

U.S. PATENT DOCUMENTS

| 926,591 A | 6/1909 | Odquist |
|---|---|---|
| 4,261,341 A | 4/1981 | Hakim |

(Continued)

FOREIGN PATENT DOCUMENTS

| CN | 101449987 A | 6/2009 |
|---|---|---|
| CN | 103260547 A | 8/2013 |

(Continued)

OTHER PUBLICATIONS

US 7,169,126 B2, 01/2007, Zadno-Azizi (withdrawn)
(Continued)

*Primary Examiner* — Brandy S Lee
*Assistant Examiner* — Avery Smale
(74) *Attorney, Agent, or Firm* — Wan Chieh Lee; Haug Partners LLP

(57) ABSTRACT

A therapeutic agent delivery system includes a catheter, a vascular occluder, a pressure sensor system, and a pump system. The vascular occluder is provided at a distal end of the catheter. The pressure sensor system is provided to sense pressure at a distal end of a catheter lumen, and provides feedback to the pump system. The pump system is adapted to control a rate of infusion of a therapeutic agent through the catheter lumen based on the pressure sensed by the pressure sensor system. A method includes deploying the vascular occluder in a vessel, and then sensing a pressure in the vessel. The therapeutic agent is infused into the vessel at a flow rate based on the sensed pressure in the vessel.

36 Claims, 4 Drawing Sheets

(51) Int. Cl.
  *A61M 5/168* (2006.01)
  *A61B 17/12* (2006.01)
  *A61B 5/0275* (2006.01)
  *A61M 25/00* (2006.01)
  *A61M 25/10* (2013.01)

(52) U.S. Cl.
  CPC ......... *A61B 5/0275* (2013.01); *A61B 17/1204* (2013.01); *A61B 17/12109* (2013.01); *A61B 17/12136* (2013.01); *A61B 17/12168* (2013.01); *A61M 2005/1726* (2013.01); *A61M 2025/0002* (2013.01); *A61M 2025/105* (2013.01); *A61M 2025/1052* (2013.01); *A61M 2205/583* (2013.01)

(58) Field of Classification Search
  CPC ................ A61M 5/1723; A61M 5/007; A61M 5/16877; A61M 2005/1726; A61M 2025/0002; A61M 2025/105; A61M 2025/1052; A61M 2205/583; A61M 25/0045; A61M 25/0074; A61M 25/0075; A61M 2210/12; A61M 2025/0004; A61M 2025/0006; A61M 2025/0175; A61M 25/10; A61M 2025/0001; A61M 2025/0076; A61M 25/0082; A61M 25/0097; A61M 2205/3331; A61M 2205/3334; A61M 2205/3344
  See application file for complete search history.

(56) References Cited

U.S. PATENT DOCUMENTS

| | | | |
|---|---|---|---|
| 4,311,587 A | 1/1982 | Nose | |
| 4,655,771 A | 4/1987 | Wallsten | |
| 4,714,460 A | 12/1987 | Calderon | |
| 4,738,740 A | 4/1988 | Pinchuk | |
| 4,800,016 A | 1/1989 | Yang | |
| 4,840,542 A | 6/1989 | Abbott | |
| 4,883,459 A | 11/1989 | Calderon | |
| 4,892,518 A | 1/1990 | Cupp | |
| 5,024,668 A * | 6/1991 | Peters | A61M 25/1002 600/18 |
| 5,030,199 A | 7/1991 | Barwick | |
| 5,071,407 A | 12/1991 | Termin | |
| 5,084,015 A | 1/1992 | Moriuchi | |
| 5,171,299 A | 12/1992 | Heitzmann | |
| 5,234,425 A | 8/1993 | Fogarty | |
| 5,397,307 A | 3/1995 | Goodin | |
| 5,397,308 A | 3/1995 | Ellis | |
| 5,411,478 A | 5/1995 | Stillabower | |
| 5,419,763 A | 5/1995 | Hildebrand | |
| 5,484,399 A | 1/1996 | DiResta et al. | |
| 5,484,412 A | 1/1996 | Pierpont | |
| 5,496,277 A | 3/1996 | Termin | |
| 5,607,466 A | 3/1997 | Imbert | |
| 5,668,237 A | 9/1997 | Popall | |
| 5,688,237 A | 11/1997 | Rozga | |
| 5,725,571 A | 3/1998 | Imbert | |
| 5,755,687 A | 5/1998 | Donlon | |
| 5,755,769 A | 5/1998 | Richard | |
| 5,759,205 A | 6/1998 | Valentini | |
| 5,810,789 A | 9/1998 | Powers | |
| 5,836,905 A | 11/1998 | Lemelson | |
| 5,836,967 A | 11/1998 | Schneider | |
| 5,893,869 A | 4/1999 | Barnhart | |
| 5,895,399 A | 4/1999 | Barbut | |
| 5,897,567 A | 4/1999 | Ressemann | |
| 5,910,154 A | 6/1999 | Tsugita | |
| 5,911,734 A | 6/1999 | Tsugita | |
| 5,957,974 A | 9/1999 | Thompson | |
| 6,001,118 A | 12/1999 | Daniel | |
| 6,010,522 A | 1/2000 | Barbut | |
| 6,027,520 A | 2/2000 | Tsugita | |
| 6,042,598 A | 3/2000 | Tsugita | |
| 6,051,014 A | 4/2000 | Jang | |
| 6,059,745 A | 5/2000 | Gelbfish | |
| 6,152,946 A | 11/2000 | Broome | |
| 6,165,199 A | 12/2000 | Barbut | |
| 6,165,200 A | 12/2000 | Tsugita | |
| 6,168,579 B1 | 1/2001 | Tsugita | |
| 6,179,851 B1 | 1/2001 | Barbut | |
| 6,231,551 B1 | 5/2001 | Barbut | |
| 6,235,044 B1 | 5/2001 | Root | |
| 6,258,120 B1 | 7/2001 | McKenzie | |
| 6,306,074 B1 | 10/2001 | Waksman | |
| 6,306,163 B1 | 10/2001 | Fitz | |
| 6,309,399 B1 | 10/2001 | Barbut | |
| 6,361,545 B1 | 3/2002 | Macoviak | |
| 6,371,969 B1 | 4/2002 | Tsugita | |
| 6,371,971 B1 | 4/2002 | Tsugita | |
| 6,383,206 B1 | 5/2002 | Gillick | |
| 6,395,014 B1 | 5/2002 | Macoviak | |
| 6,416,495 B1 | 7/2002 | Kriesel | |
| 6,436,112 B2 | 8/2002 | Wensel | |
| 6,443,926 B1 | 9/2002 | Kletschka | |
| 6,478,783 B1 | 11/2002 | Moorehead | |
| 6,485,456 B1 | 11/2002 | Kletschka | |
| 6,485,502 B2 | 11/2002 | Don Michael | |
| 6,499,487 B1 | 12/2002 | McKenzie | |
| 6,500,203 B1 | 12/2002 | Thompson | |
| 6,520,183 B2 | 2/2003 | Amar | |
| 6,530,935 B2 | 3/2003 | Wensel | |
| 6,533,800 B1 | 3/2003 | Barbut | |
| 6,537,294 B1 | 3/2003 | Boyle | |
| 6,537,297 B2 | 3/2003 | Tsugita | |
| 6,540,722 B1 | 4/2003 | Boyle | |
| 6,551,303 B1 | 4/2003 | Van Tassel | |
| 6,565,552 B1 | 5/2003 | Barbut | |
| 6,569,146 B1 | 5/2003 | Werner | |
| 6,582,396 B1 | 6/2003 | Parodi | |
| 6,589,264 B1 | 7/2003 | Barbut | |
| 6,592,546 B1 | 7/2003 | Barbut | |
| 6,607,506 B2 | 8/2003 | Kletschka | |
| 6,620,148 B1 | 9/2003 | Tsugita | |
| 6,635,070 B2 | 10/2003 | Leeflang | |
| 6,641,553 B1 | 11/2003 | Chee | |
| 6,641,572 B2 | 11/2003 | Cherkassky | |
| 6,645,220 B1 | 11/2003 | Huter | |
| 6,645,222 B1 | 11/2003 | Parodi | |
| 6,645,223 B2 | 11/2003 | Boyle | |
| 6,652,555 B1 | 11/2003 | VanTassel | |
| 6,652,556 B1 | 11/2003 | VanTassel | |
| 6,656,351 B2 | 12/2003 | Boyle | |
| 6,673,090 B2 | 1/2004 | Root | |
| 6,676,682 B1 | 1/2004 | Tsugita | |
| 6,689,150 B1 | 2/2004 | VanTassel | |
| 6,692,508 B2 | 2/2004 | Wensel | |
| 6,692,509 B2 | 2/2004 | Wensel | |
| 6,692,513 B2 | 2/2004 | Streeter | |
| 6,695,813 B1 | 2/2004 | Boyle | |
| 6,695,858 B1 | 2/2004 | Dubrul | |
| 6,699,231 B1 | 3/2004 | Sterman | |
| 6,702,834 B1 | 3/2004 | Boylan | |
| 6,706,053 B1 | 3/2004 | Boylan | |
| 6,706,055 B2 | 3/2004 | Douk | |
| 6,730,108 B2 | 5/2004 | VanTassel | |
| 6,743,196 B2 | 6/2004 | Barbut | |
| 6,746,469 B2 | 6/2004 | Mouw | |
| 6,746,489 B2 | 6/2004 | Dua | |
| 6,802,317 B2 | 10/2004 | Goebel | |
| 6,818,006 B2 | 11/2004 | Douk | |
| 6,830,579 B2 | 12/2004 | Barbut | |
| 6,837,898 B2 | 1/2005 | Boyle | |
| 6,855,154 B2 | 2/2005 | Abdel-Gawwad | |
| 6,866,677 B2 | 3/2005 | Douk | |
| 6,887,258 B2 | 5/2005 | Denison | |
| 6,896,690 B1 | 5/2005 | Lambrecht | |
| 6,902,540 B2 | 6/2005 | Dorros | |
| 6,908,474 B2 | 6/2005 | Hogendijk | |
| 6,911,036 B2 | 6/2005 | Douk | |
| 6,936,060 B2 | 8/2005 | Hogendijk | |
| 6,939,362 B2 | 9/2005 | Boyle | |

(56) References Cited

U.S. PATENT DOCUMENTS

| | | | |
|---|---|---|---|
| 6,964,670 B1 | 11/2005 | Shah |
| 6,964,673 B2 | 11/2005 | Tsugita |
| 6,974,469 B2 | 12/2005 | Broome |
| 6,989,027 B2 | 1/2006 | Allen |
| 6,997,898 B2 | 2/2006 | Forman |
| 7,044,958 B2 | 5/2006 | Douk |
| 7,044,966 B2 | 5/2006 | Svanidze |
| 7,066,946 B2 | 6/2006 | Douk |
| 7,101,396 B2 | 9/2006 | Artof |
| 7,118,600 B2 | 10/2006 | Dua |
| 7,162,303 B2 | 1/2007 | Levin |
| 7,169,164 B2 | 1/2007 | Borillo |
| 7,172,614 B2 | 2/2007 | Boyle |
| 7,172,621 B2 | 2/2007 | Theron |
| 7,214,237 B2 | 5/2007 | Don Michael |
| 7,217,255 B2 | 5/2007 | Boyle |
| 7,223,253 B2 | 5/2007 | Hogendijk |
| 7,232,452 B2 | 6/2007 | Adams |
| 7,232,453 B2 | 6/2007 | Shimon |
| 7,241,304 B2 | 7/2007 | Boyle |
| 7,250,041 B2 | 7/2007 | Chiu |
| 7,252,675 B2 | 8/2007 | Denison |
| 7,279,000 B2 | 10/2007 | Cartier |
| 7,306,575 B2 | 12/2007 | Barbut |
| 7,322,957 B2 | 1/2008 | Kletschka |
| 7,326,226 B2 | 2/2008 | Root |
| 7,331,973 B2 | 2/2008 | Gesswein |
| 7,338,510 B2 | 3/2008 | Boylan |
| 7,344,549 B2 | 3/2008 | Boyle |
| 7,364,566 B2 | 4/2008 | Elkins |
| 7,371,249 B2 | 5/2008 | Douk |
| 7,425,215 B2 | 9/2008 | Boyle |
| 7,503,904 B2 | 3/2009 | Choi |
| 7,537,600 B2 | 5/2009 | Eskuri |
| 7,544,202 B2 | 6/2009 | Cartier |
| 7,572,272 B2 | 8/2009 | Denison |
| 7,582,100 B2 | 9/2009 | Johnson |
| 7,585,309 B2 | 9/2009 | Larson |
| 7,591,832 B2 | 9/2009 | Eversull |
| 7,604,650 B2 | 10/2009 | Bergheim |
| 7,647,115 B2 | 1/2010 | Levin |
| 7,653,438 B2 | 1/2010 | Deem |
| 7,658,747 B2 | 2/2010 | Forde |
| 7,686,781 B2 | 3/2010 | Vinten-Johansen |
| 7,833,242 B2 | 11/2010 | Gilson |
| 7,842,084 B2 | 11/2010 | Bicer |
| 7,846,139 B2 | 12/2010 | Zinn |
| 7,853,333 B2 | 12/2010 | Demarais |
| 7,873,417 B2 | 1/2011 | Demarais |
| 7,922,691 B2 | 4/2011 | Kletchka |
| 7,935,075 B2 | 5/2011 | Tockman |
| 7,937,143 B2 | 5/2011 | Demarais |
| 7,938,799 B2 | 5/2011 | Epstein |
| 7,993,324 A9 | 8/2011 | Barbut |
| 8,162,879 B2 | 4/2012 | Hattangadi |
| 8,172,792 B2 | 5/2012 | Wang |
| 8,182,446 B2 | 5/2012 | Schaeffer |
| 8,200,312 B2 | 6/2012 | Degani |
| 8,251,948 B2 | 8/2012 | Goldman |
| 8,257,384 B2 | 9/2012 | Bates |
| 8,262,611 B2 | 9/2012 | Teesllink |
| 8,397,578 B2 | 3/2013 | Miesel |
| 8,409,166 B2 | 4/2013 | Wiener |
| 8,500,775 B2 | 8/2013 | Chomas |
| 8,696,698 B2 | 4/2014 | Chomas |
| 8,696,699 B2 | 4/2014 | Chomas |
| 8,821,476 B2 | 9/2014 | Agah |
| 8,852,207 B2 | 10/2014 | Simpson |
| 9,023,010 B2 | 5/2015 | Chiu |
| 9,061,117 B2 | 6/2015 | Roberts |
| 9,078,982 B2 | 7/2015 | Lane |
| 9,089,341 B2 | 7/2015 | Chomas |
| 9,126,016 B2 | 9/2015 | Chomas |
| 9,174,020 B2 | 11/2015 | Allen |
| 9,205,226 B2 | 12/2015 | Allen |
| 9,265,914 B2 | 2/2016 | Fulton, III |
| 9,364,358 B2 | 6/2016 | Cohen |
| 9,457,171 B2 | 10/2016 | Agah |
| 9,463,304 B2 | 10/2016 | Agah |
| 9,474,533 B2 | 10/2016 | Mathis |
| 9,539,081 B2 | 1/2017 | Chomas |
| 9,550,046 B1 | 1/2017 | Allen |
| 9,597,480 B2 | 3/2017 | Purdy |
| 9,604,037 B2 | 3/2017 | Fischer, Jr. |
| 9,737,693 B2 | 8/2017 | Helkowski |
| 9,770,319 B2 | 9/2017 | Pinchuk |
| 9,808,332 B2 | 11/2017 | Chomas |
| 9,844,383 B2 | 12/2017 | Allen |
| 9,913,959 B2 | 3/2018 | Purdy |
| 9,968,740 B2 | 5/2018 | Pinchuk |
| 10,092,742 B2 | 10/2018 | Genstler |
| 10,099,040 B2 | 10/2018 | Agah |
| 10,130,762 B2 | 11/2018 | Allen |
| 11,324,619 B1 | 5/2022 | Yacoby |
| 2001/0041862 A1 | 11/2001 | Glickman |
| 2002/0042593 A1 | 4/2002 | Mickley |
| 2002/0161390 A1 | 10/2002 | Mouw |
| 2002/0161394 A1 | 10/2002 | Macoviak |
| 2003/0097114 A1 | 5/2003 | Duriel |
| 2003/0125790 A1 | 7/2003 | Fastovsky |
| 2003/0187474 A1 | 10/2003 | Keegan |
| 2003/0212361 A1 | 11/2003 | Boyle |
| 2003/0233115 A1 | 12/2003 | Eversull |
| 2004/0006305 A1 | 1/2004 | Hebert |
| 2004/0054315 A1 | 3/2004 | Levin |
| 2004/0068288 A1 | 4/2004 | Palmer |
| 2004/0143185 A1 | 7/2004 | Zatezalo |
| 2004/0215142 A1 | 10/2004 | Matheis |
| 2004/0220511 A1 | 11/2004 | Scott |
| 2004/0220521 A1 | 11/2004 | Barbut |
| 2004/0220609 A1 | 11/2004 | Douk |
| 2004/0225354 A1 | 11/2004 | Allen |
| 2004/0256584 A1 | 12/2004 | Zimmerling |
| 2004/0260333 A1 | 12/2004 | Dubral |
| 2005/0004517 A1 | 1/2005 | Courtney |
| 2005/0010285 A1 | 1/2005 | Lambrecht |
| 2005/0015048 A1 | 1/2005 | Chiu |
| 2005/0015112 A1 | 1/2005 | Cohn |
| 2005/0113798 A1* | 5/2005 | Slater .................... A61M 25/10 606/213 |
| 2005/0119688 A1 | 6/2005 | Burgheim |
| 2005/0149112 A1 | 7/2005 | Barbut |
| 2005/0261759 A1 | 11/2005 | Lambrecht |
| 2006/0124140 A1 | 6/2006 | Forsell |
| 2006/0167537 A1 | 7/2006 | Larsson |
| 2006/0173490 A1 | 8/2006 | LaFontaine |
| 2006/0177478 A1 | 8/2006 | Humes |
| 2006/0263301 A1 | 11/2006 | Vernon |
| 2006/0264898 A1 | 11/2006 | Beasley |
| 2007/0106258 A1 | 5/2007 | Chiu |
| 2007/0106324 A1 | 5/2007 | Gamer |
| 2007/0179590 A1 | 8/2007 | Lu |
| 2007/0239135 A9 | 10/2007 | Barbut |
| 2008/0031740 A1 | 2/2008 | Miyazaki |
| 2008/0031962 A1 | 2/2008 | Boyan |
| 2008/0033341 A1 | 2/2008 | Grad |
| 2008/0039786 A1 | 2/2008 | Epstein |
| 2008/0051758 A1 | 2/2008 | Rioux |
| 2008/0097273 A1 | 4/2008 | Levin |
| 2008/0103523 A1 | 5/2008 | Chiu |
| 2008/0147007 A1 | 6/2008 | Freyman |
| 2008/0234796 A1 | 9/2008 | Dorn |
| 2009/0018498 A1 | 1/2009 | Chiu |
| 2009/0076409 A1 | 3/2009 | Wu |
| 2009/0088676 A1 | 4/2009 | Murata |
| 2009/0198321 A1 | 8/2009 | Sutermeister |
| 2009/0222035 A1 | 9/2009 | Schneiderman |
| 2009/0234266 A1 | 9/2009 | Solomon |
| 2009/0234283 A1 | 9/2009 | Burton |
| 2009/0264819 A1 | 10/2009 | Diethrich |
| 2010/0168785 A1 | 7/2010 | Parker |
| 2010/0331815 A1 | 12/2010 | Alt |
| 2011/0046542 A1 | 2/2011 | Evans |
| 2011/0130657 A1 | 6/2011 | Chomas |

(56) References Cited

U.S. PATENT DOCUMENTS

| | | | |
|---|---|---|---|
| 2011/0137399 | A1 | 6/2011 | Chomas |
| 2011/0218494 | A1 | 9/2011 | Gerrans |
| 2011/0288529 | A1 | 11/2011 | Fulton |
| 2011/0295114 | A1 | 12/2011 | Agah |
| 2011/0295203 | A1 | 12/2011 | Hayes |
| 2012/0116351 | A1 | 5/2012 | Chomas |
| 2012/0259206 | A1 | 10/2012 | Roberts |
| 2013/0079731 | A1 | 3/2013 | Chomas |
| 2013/0116655 | A1 | 5/2013 | Bacino |
| 2013/0226166 | A1 | 8/2013 | Chomas |
| 2014/0066830 | A1 | 3/2014 | Lad |
| 2014/0073536 | A1 | 3/2014 | Lin |
| 2014/0207178 | A1 | 7/2014 | Chomas |
| 2014/0276135 | A1 | 9/2014 | Agah |
| 2014/0276411 | A1 | 9/2014 | Cowan |
| 2014/0364835 | A1* | 12/2014 | Allen ............... A61M 25/0075 604/102.03 |
| 2014/0378951 | A1 | 12/2014 | Dye |
| 2015/0272716 | A1 | 10/2015 | Pinchuk |
| 2015/0306311 | A1 | 10/2015 | Pinchuk |
| 2016/0015508 | A1* | 1/2016 | Chomas ............... A61F 2/013 606/200 |
| 2016/0015948 | A1 | 1/2016 | Agah |
| 2016/0045316 | A1 | 2/2016 | Braido et al. |
| 2016/0074633 | A1 | 3/2016 | Schaffner |
| 2016/0082178 | A1 | 3/2016 | Agah |
| 2016/0206798 | A1 | 7/2016 | Williams et al. |
| 2016/0235942 | A1 | 8/2016 | Alt |
| 2016/0235950 | A1 | 8/2016 | Murata |
| 2016/0249969 | A1 | 9/2016 | Santoinanni |
| 2016/0256626 | A9 | 9/2016 | Chomas |
| 2016/0310148 | A1 | 10/2016 | Allen |
| 2017/0000493 | A1 | 1/2017 | Boehm, Jr. |
| 2017/0049946 | A1 | 2/2017 | Kapur |
| 2017/0056629 | A1 | 3/2017 | Agah |
| 2017/0157370 | A1 | 6/2017 | Agah |
| 2017/0173309 | A1 | 6/2017 | Fischer, Jr. |
| 2017/0189654 | A1* | 7/2017 | Schwartz ............. A61B 5/0215 |
| 2017/0209666 | A1 | 7/2017 | Quigley |
| 2017/0319820 | A1 | 11/2017 | Johnson |
| 2017/0368306 | A1 | 12/2017 | Tal |
| 2018/0055620 | A1 | 1/2018 | Chomas |
| 2018/0116522 | A1 | 5/2018 | Brenneman |
| 2018/0125502 | A1 | 5/2018 | Allen |
| 2018/0250469 | A1 | 9/2018 | Pinchuk |
| 2018/0263752 | A1 | 9/2018 | Pinchuk |
| 2018/0289464 | A1 | 10/2018 | Kassab |
| 2018/0333563 | A1 | 11/2018 | Agah |
| 2019/0046157 | A1 | 2/2019 | Unser |
| 2019/0083705 | A1 | 3/2019 | Allen |
| 2020/0038586 | A1 | 2/2020 | Chomas et al. |
| 2020/0078555 | A1 | 3/2020 | Agah |
| 2020/0108239 | A1 | 4/2020 | Arepally et al. |
| 2020/0205840 | A1 | 7/2020 | Adawi |
| 2020/0261695 | A1 | 8/2020 | Jaroch et al. |
| 2020/0383688 | A1 | 12/2020 | Olson |
| 2021/0244473 | A1 | 8/2021 | Cook |
| 2021/0338976 | A1 | 11/2021 | Jaroch et al. |

FOREIGN PATENT DOCUMENTS

| | | |
|---|---|---|
| CN | 203107204 U | 8/2013 |
| CN | 105007973 A | 10/2015 |
| CN | 105208946 A | 12/2015 |
| DE | 8910603 U1 | 12/1989 |
| EP | 0416662 B1 | 3/1991 |
| EP | 0533511 A1 | 3/1993 |
| EP | 0554579 A1 | 8/1993 |
| EP | 1226795 | 7/2002 |
| EP | 1527740 | 5/2005 |
| EP | 1743524 | 1/2007 |
| EP | 1803423 | 7/2007 |
| EP | 2359893 A1 | 8/2011 |
| FR | 2652267 A1 | 3/1991 |
| GB | 2020557 B | 11/1979 |
| JP | 2006051144 A | 2/2006 |
| JP | 2006523515 | 10/2006 |
| WO | 8905667 | 6/1989 |
| WO | 9902093 A1 | 1/1999 |
| WO | 199916382 | 4/1999 |
| WO | 199944510 A1 | 9/1999 |
| WO | 200141679 | 6/2001 |
| WO | 200145592 | 6/2001 |
| WO | 200149215 A2 | 7/2001 |
| WO | 0197879 | 12/2001 |
| WO | 02055146 A1 | 7/2002 |
| WO | 2004043293 | 5/2004 |
| WO | 2004075776 | 9/2004 |
| WO | 2011068946 | 6/2011 |
| WO | 2016149653 | 9/2016 |
| WO | 2019140381 A1 | 7/2019 |

OTHER PUBLICATIONS

Search Report and Written Opinion dated Jan. 6, 2020 of application No. PCT/US 19/54406.
A Study of the Geometrical and Mechanical Properties of a Self-Expandig Metallic Stent Theory and Experiment, Dr. Michael R. Jedwab, Claude 0. Clerc, Journal of Applied Biomaterials, vol. 4, Issue 1, pp. 77-85, Spring 1993.
U.S. Appl. No. 61/266,068, filed Dec. 2, 2009, Chomas et al.
U.S. Appl. No. 61/382,290, filed Sep. 13, 2010, Chomas et al.
Catheter-Based Renal Sympathetic Denervation for Resistant Hypertension: a Multicentre Safety and Proof-of-Principle Cohort Study, Krum et al, The Lancet, 2009.
Embolization II, Scientific Session 11, JVIR, Mar. 27, 2012.
Embolization procedure lowers levels of "hunger hormone," leads to weight loss, EurekAlert Public Release, Mar. 7, 2013.
Finite Element Stent Design, M. De Beule, R. Van Impe, P. Verdonck, B. Verhegghe, Computer Methods in Biomechanics and Biomedical Engineering, 2005.
First-In-Man Study of Left Gastric Artery Embolization for Weight Loss, Nicholas Kipshidze et al., ACC.13, E2056, UACC Mar. 12, 2013, vol. 61, Issue 10.
Fusion Drug Delivery System—Novel Catheter/Stent Design for Targeted Drug Delivery, Gerschwind & Barnett, Non-Published US provisional patent application filed Sep. 17, 2007.
Left Gastric Embolization Leads to Weight Loss, Bariatriac News, Owen Haskins, Dec. 4, 2013.
Renal Denervation as a Therapeutic Approach for Hypertension: Novel Implications for an Old Concept, Schlaich et al., Hypertension, Journal of the American Heart Association, 2009, 54:1195-1201.
Renal Sympathetic-Nerve Ablation for Uncontrolled Hypertension, Schlaich et al, The New England Journal of Medicine, 2009, pp. 932-934, Aug. 27, 2009.
International Search Report of PCT/US18/22171 dated Aug. 3, 2018.
International Search Report and Written Opinion of Application No. PCT/US16/23723 dated Sep. 2, 2016.
Allogenic Chimeric Antigen Receptor-Modified Cells for Adoptive Cell Therapy of Cancer, Marcus, Assaf et al., Mar. 24, 2014, Expert Opinion of Biological Therapy, vol. 14, Issue 7.
RenovoCath(tm) RC120 The Future of Targeted Delivery, RenovoRx Inc., web brochure downloaded from Internet on Feb. 2, 2015.
Cannulation of the Cardiac Lymphatic Sytem in Swine, Vazquez-Jiminez et al., European Journal of Cardio-thoracic Surgery 18 (2000) 223-232.
Development of Repeatable Microcatheter Access Port for Intra-arterial Therapy of Liver Cancer, Yasushi Fukuoka et al., Cardiovasc Intervent Radiol (2019) 42:298-303.
Long-Term Catheterization of the Intestinal Lymph Trunk and Collection of Lymph in Neonatal Pigs, Richard R. Uwiera et al., Journal of Visualized Experiments, Mar. 2016, 109, e53457.
Lymphaniography to Treat Postoperative Lymphatic Leakage: A Technical Review, Edward Wolfgang Lee, et al., Korean Journal of Radiology 15(6), Nov./Dec. 2014.

(56) References Cited

OTHER PUBLICATIONS

Radiologic Placement of Side-hole Catheter with Tip Fixation for Hepatic Arterial Infusion Chemotherapy, Toshihiro Tanaka et al., J Vasc Interv Radiol 2003: 14:63-68.

Superselective Retrograde Lymphatic Duct Embolization for Management of Postoperataive Lymphatic Leak, Bulent Arslan et al., Diagn Interv Radiol 2017; 23:379-380.

International Search Report and Written Opinion of Application No. PCT/US19/13482 dated Jun. 10, 2019.

Estimation of Tumor Interstitial Fluid Pressure (TIFP) Noninvasively, Long Lian Liu et al., PLOS One | DOI:10.1371/journal.pone.0140892 Jul. 28, 2016.

EP Search Report and Written Opinion of Application No. EP19739019 dated Sep. 17, 2021.

Chinese Office Action and Search Report dated Jan. 10, 2022 of Application No. 201980016342.3.

U.S. Appl. No. 15/871,326, filed Jan. 15, 2018, Arepally et al.
U.S. Appl. No. 17/375,779, filed Jul. 14, 2021, Arepally et al.
U.S. Appl. No. 17/671,296, filed Feb. 14, 2022, Arepally et al.

Japanese Office Action dated Apr. 28, 2021 of Application No. 2020-082002.

Canadian Office Action 2 dated Jun. 3, 2022 of Application No. 3,139,118.

International Search Report and Written Opinion of Application No. PCT/US2020/034626 dated Aug. 26, 2020.

Japanese Office Action dated May 10, 2022 of Application No. 2021-572025.

\* cited by examiner

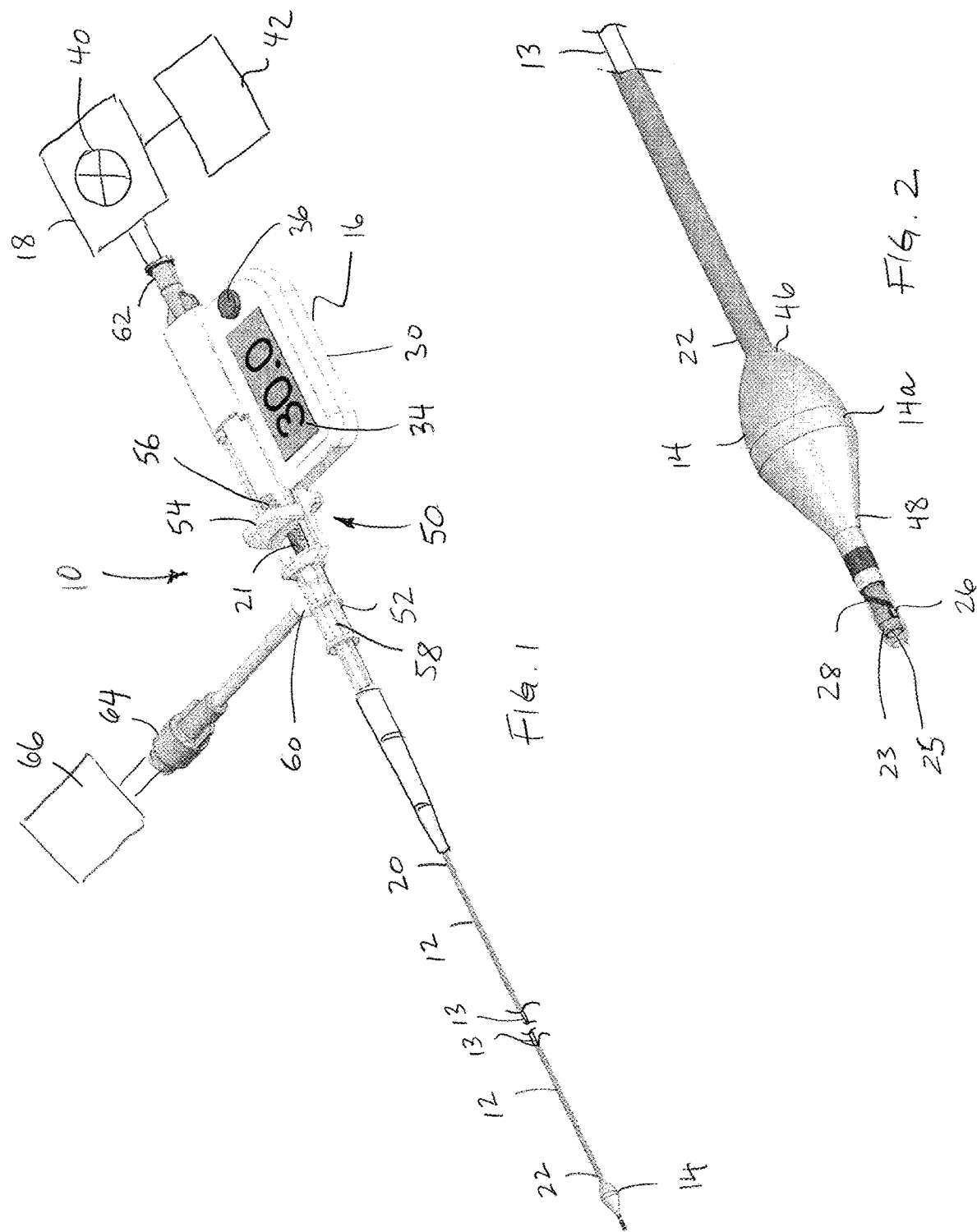

SYSTEMS AND METHODS FOR PRESSURE-FACILITATED THERAPEUTIC AGENT DELIVERY

CROSS-REFERENCE TO RELATED APPLICATIONS

This application claims benefit from U.S. Ser. No. 62/713,410, filed Aug. 1, 2018, which is hereby incorporated by reference herein in its entirety.

BACKGROUND OF THE INVENTION

1. Field of the Invention

The medical devices and methods described herein relate generally to devices and methods for infusing a therapeutic agent through a vessel to a target tissue for the treatment of cancers or other diseases.

2. State of the Art

Systemic treatments have been used to treat disease within a patient. The effectiveness of some such systemic treatments can vary due at least in part to the treatment (e.g., a radio-embolization agent, a biologic agent and/or other treatment formulation) not reaching target tissue. For example, in the treatment of some diseases such as pancreatic cancer, it may be desirable to deliver biological cells to the pancreas where efficient and safe engraftment can be achieved, especially to the pancreatic tail, for example, where a large number of the endogenous islet cells reside.

A treatment can include transplanting such cells into the pancreas itself. For example, one treatment has included sub-selective endovascular injection of cells into the arterial supply of the pancreatic tissue. Such an approach, however, is subject to variation in the number of cells actually introduced to the pancreas (versus other organs in the same vascular bed including the spleen, the liver, and/or the stomach). Furthermore, inadvertent exposure of other non-target organs to such cells can result in health risks for the patient.

Moreover, pancreatic cancer is considered an almost chemoresistant tumor. The ineffective result of systemic chemotherapy is at least in part due to an insufficient drug concentration within the tumor because of dose-limited toxicity in bone marrow and epithelial tissue. Since systemic chemotherapy is limited in its effectiveness, treatments beyond systemic chemotherapy can be desirable for advanced pancreatic cancer patients. For example, one such treatment can include local intra-arterial delivery of chemotherapy. Intra-arterial infusion allows higher drug concentration to reach the tumor. Furthermore, intra-arterial chemotherapy can also take advantage of the first pass effect of chemotherapeutics, generating higher-level drug concentrations at the tumor cell membrane and therefore, enhancing cellular drug uptake as compared to intravenous infusion. Lastly, local delivery can reduce systemic side effects.

Intra-arterial chemotherapy treatment to the pancreas is usually administered through small catheters placed in the pancreatic arteries arising from the splenic artery or gastroduodenal artery. An issue in catheter localization is the redundant nature of blood supply to the pancreas overlaps adjacent organs. Furthermore, the small size and anatomical variability of the branches of the splenic arteries to the pancreas precludes reproducible cannulization via interventional techniques. Delivering the therapeutic agent to the correct location requires knowledge of the patient's specific arterial anatomy, preferably obtained through visualization techniques in advance of therapeutic delivery of the treatment.

Even then, standard catheters permit limited control of the infused treatment. The treatment will flow from an area of high pressure to an area of lower pressure. Given the cyclic pressures operating on the blood as the heart beats, the treatment can reflux into healthy tissues where it will do harm, rather than good. Tumors in the pancreas and most solid tumors often are higher pressure than the mean arterial pressure due to multiple mechanisms in the tumor microenvironment, and these tumors are not perfused or poorly perfused from the arterial supply. Infusion with a standard catheter cannot increase pressure or flow in downstream territory, and therefore cannot improve delivery into the tumor.

Similar issues apply to the infusion of treatment agents for the treatment of liver and kidney cancers. That is, chemotherapy has been often ineffective at least in part due to an insufficient therapy concentration within the tumor because of dose-limited toxicity; thus, doses are limited to a level that reduces localized concentrations available for cellular-level tumor uptake and, consequently, a resultant opportunity for positive results.

In order to alleviate certain of these issues, co-owned U.S. Pat. No. 8,696,698 to Chomas describes a pressure-facilitated therapeutic delivery device in the form of a microvalve mounted at the distal end of catheter. The microvalve dynamically expands and contracts within a blood vessel in relation to the surrounding blood pressure. A treatment can be infused through the catheter under pressure generated by a hand-operated syringe. When the therapeutic agent is infused, the pressure in the vessel causes the microvalve to open and block reflux of the agent. Alternatively, the therapeutic agent can be infused under a relatively low pressure, and a follow-on bolus of saline can be manually injected into the catheter after the therapeutic agent to generate the relatively higher pressure in the vessel that is anticipated to result in target tissue penetration. Nevertheless, these syringe-infused elevated pressures, clinically speaking, are relatively low pressure treatments and have limits on their ability for concentration of the therapeutic agent at the target site.

SUMMARY OF THE INVENTION

A therapeutic agent delivery system is provided for the treatment of an organ with a vascular-infused therapeutic agent. In an embodiment, the delivery system includes a catheter, a vascular occluder, a pressure sensor system, and a pump system. The catheter has a proximal end, a distal end, and a lumen extending between the proximal and distal ends. The vascular occluder is provided at the distal end of the catheter. The pressure sensor system is provided to sense pressure at the distal end of the catheter and within the lumen, and provides feedback to the pump system. The pump system is adapted to automatically control the rate of infusion of the therapeutic agent through the lumen of the catheter based on the pressure sensed by the pressure sensor system.

In embodiments of the system, the vascular occluder can be static or dynamic. A static occluder includes a fluid inflatable balloon, a self-expanding or manually expandable filter, and a mechanically expandable malecot catheter. These elements cause occlusion of the vessel by being sufficiently expanded to block flow within a vessel around a static occluder, and do not modulate in expansion in view of localized fluid pressure conditions within the vessel. A dynamic occluder is automatically and dynamically movable based on localized fluid pressure conditions about proximal and distal surfaces of the occluder. Such a dynamic occluder includes, by way of example, a microvalve that automatically expands to the diameter of the vessel in which it is deployed when subjected to predetermined fluid pressure conditions and contracts to a smaller diameter away from the vessel wall when subject to relatively lower fluid pressure conditions. A microvalve suitable for use preferably includes self-expanding filamentary braid having a frusto-conical portion with a low radial force of expansion and covered with a fabric or membrane. The fabric or membrane may be microporous or a non-porous polymer and can be formed by electrospinning or dip-coating a polymer over a filamentary braid.

In embodiments of the system, the pressure sensor system includes a pressure sensor in communication with the lumen of the catheter. In embodiments, the pressure sensor system includes a pressure sensor located at the distal end of the catheter. The pressure sensor preferably provides real-time feedback to the pump system and to a display that displays the measured pressure. In an embodiment, the catheter is provided with a proximal handle, and the display is located on the handle.

The pump system includes an infusion pump or injector (hereinafter, collectively 'pump') adapted to infuse the therapeutic agent with a controlled flow rate that can achieve significantly higher flow rates than manual injection permits such that high pressures can be generated in the vessel. Such generated pressures allow the therapy to overcome the high pressure tumor microenvironment, higher concentrations of therapeutic agent to be delivered to the target tissue, and higher residence time of therapeutic agent to be maintained in the target tissue to increase binding time of the therapeutic agent to the target tissue. The infusion pump communicates with the pressure sensor and is adapted, based on feedback from the pressure sensor, to automatically inject the therapeutic agent at higher (or, if necessary, lower) flow rates until a determined minimum pressure is reached or maintained during delivery of the dose of the therapeutic agent.

Using the system, models have been identified that permit delivery of the therapeutic agent to specific identified organs at respective delivery rates that generate significantly high pressures within the vessel and which results in overcoming the flow resistance, permit a desirable level of therapeutic agent concentration in the tissue, and provide an enhanced dwell time of the therapeutic agent in the tissue.

The system may be used in various methods to provide the therapeutic agent to a localized region within a patient; i.e., a selected organ. The system may be used in either a venous or arterial approach, preferably in a manner that most benefits delivery of the therapeutic agent under pressure to a particular target tissue. The system and its use prevent or at least minimize systemic circulation of the therapeutic agent.

According to one method of use, the system is provided. The distal end of the catheter is advanced to a deployment site in a vessel within a target organ or adjacent a target tissue. Depending on the target organ or target tissue for treatment, the catheter can be advanced through an arterial pathway or a venous pathway to the target. The occluder is advanced in a non-deployed configuration in which the occluder is in a collapsed reduced diameter state. Once the occluder is at the deployment site and prior to its deployment, the pressure sensor is utilized to measure the pressure in the vessel at the deployment site.

The occluder is then deployed into a deployed configuration. For a static occluder in an arterial or venous pathway, the deployed configuration is a radially expanded configuration that blocks all endogenous flow in the vessel. For a dynamic occluder in an arterial pathway, the deployed configuration blocks only a limited percentage of the endogenous flow in the vessel and permits a remaining percentage of the endogenous flow in the vessel. Using a dynamic occluder in an arterial pathway, the permitted endogenous flow is preferably at least 50%, more preferably greater than 65%, and even more preferably greater than 75%. For a dynamic occluder in a venous pathway, the occluder in the deployed configuration when acted upon by the antegrade pressure of the endogenous flow causes the occluder to expand completely to the vessel wall and block substantially all of the endogenous flow in the vessel. It should be recognized that such endogenous venous flow is opposite the endogenous arterial flow, and has a different effect on intravascular pressure when deployed. After deployment of the occluder, the pressure sensor is again utilized to measure the pressure in the vessel distal of the deployment site.

The pump is then operated to inject the therapeutic agent through the lumen of the catheter and distal of the occluder at increasing flow rates until the pressure sensor senses that a determined minimum pressure above a baseline pressure is reached. The determined minimum pressure is set based on the organ or tissue being treated as well as the underlying disease characteristics such as tumor size, tumor type, or information gained from medical imaging of the tumor such as CT, CT angiography, PET, MR, Diffusion weighted MR or other modality that can characterize the relative perfusion flow and pressure in a target tumor. The flow rate of therapeutic agent from the pump is then maintained or modulated to keep the pressure in the vessel elevated to at least the minimum pressure above baseline for the duration of the dose delivery. It is recognized that for delivery of a therapeutic agent in an arterial pathway, the pressure in the vessel is related to both the endogenous flow and the infused flow. For a static occluder, the endogenous arterial flow is minimal; the generated pressure is primarily from the infused therapeutic agent. Thus, the infusion pump must produce substantially all of the fluid flow to generate the desired intravascular pressures. For a dynamic occluder, the flow in the vessel is the permitted endogenous blood flow when the occluder is deployed in addition to the infused flow. For one preferred dynamic occluder, the endogenous flow is 85% of normal blood flow in the vessel. Thus, the total fluid flow in the vessel is from 85% of normal blood flow in addition to the infused flow. As this total fluid flows within the resistive environment of the vessel, the pressure is generated, and sensed by the pressure sensor. It is further recognized that for delivery of a therapeutic agent in a venous pathway, idealized static and dynamic occluders operate in the same manner, blocking all endogenous flow. However, because the infusion of the therapeutic agent is now opposite the endogenous flow, all of the blocked endogenous flow generates pressure on the distal side of the occluder. In addition, the flow of the infused therapeutic agent is modulated to generate additional pressure so that the pressure exceeds at least the determined minimum pressure above the baseline for the duration of the therapeutic dose.

As stated above, in methods of delivering the therapeutic agent under enhanced pressure to an organ, the minimum pressure above the baseline pressure to overcome a flow resistance of the therapeutic agent through a vessel of a tumor of an organ is determined. The minimum pressure for each of the tumorous organs may be determined from one or more human study, animal study, bench model, computer simulation, and/or combinations of one or more of the aforementioned. As such, the minimum pressure can be determined from a pre-established set of data, e.g., organized in a stored database of values, such as a look-up table based on the organ. Further, the minimum pressure can be determined from characterizing of the tumor of the organ, using, e.g., imaging. In addition, the total infusion time and total therapeutic dose can be determined from characterizing of the tumor of the organ, using, e.g., imaging.

The flow resistance can also be calculated as pressure generated in the vessel divided by the fluid flow rate within the vessel. The flow rate is generated by any endogenous flow in addition to therapy infused by the pump. The pressure generated upon such flow can be directly and instantly measured by the sensor. Thus, the resistance to flow is calculated by dividing the measured pressure by the fluid flow rate. This provides an instantaneous resistance, which may or may not necessarily be accurate at all times. Therefore it may be desirable to normalize the measured resistance. To do so, multiple flow resistances can be calculated and then averaged.

Based on the (normalized) flow resistance, the therapeutic agent is infused at a flow rate into the tumor such that the minimum pressure is exceeded. In various embodiments, the minimum pressure may be exceeded by a pressure of at least 0 mmHg, and more preferably a pressure in excess of the minimum pressure that is within a range of pressures (upper and lower limits) that is specific to the tumorous organ being treated. The infusion flow rate is increased at least until a measured pressure corresponding to the intravascular pressure at the site of therapeutic delivery is within the range of pressures determined to be suitable for a tumor type, specific organ, and/or therapy. Once such flow rate is reached, the flow rate may remain constant or may be varied, preferably remaining within the range of pressures, and such that the minimum pressure is exceeded during remaining delivery of the therapeutic agent. Infusion of the therapeutic agent via the automated pump delivers higher and more consistent flow rates than achievable via a manual injection device, such as a syringe. Such infusion process permits improved efficacy, consistency and reliability for patient treatment relative to prior treatments.

In another method of delivering a therapeutic agent under enhanced pressure, the minimum pressure to overcome a flow resistance through a tumor of an organ is predetermined, and the therapeutic agent is infused at a flow rate into the tumor such that the minimum pressure is exceeded. In various embodiments, the minimum pressure may be exceeded by a pressure exceeding at least 0 mmHg relative to a baseline minimum pressure, and more preferably a pressure within a range of pressures that is specific to the tumorous organ being treated. The infusion flow rate is increased at least until a measured pressure corresponding to the intravascular pressure at the site of therapeutic delivery is within a range of pressures determined to be suitable for a tumor type, specific organ, and/or therapy. Once such flow rate is reached, the flow rate may remain constant or may be varied, preferably within the range, and such that the minimum pressure is exceeded during remaining delivery of the therapeutic agent. Such infusion process permits improved efficacy, consistency and reliability for patient treatment.

BRIEF DESCRIPTION OF THE DRAWINGS

FIG. 1 is a perspective view of a therapeutic treatment system.

FIG. 2 is an enlarged perspective view of the distal end of the therapeutic treatment system of FIG. 1.

DETAILED DESCRIPTION

Figure 3:
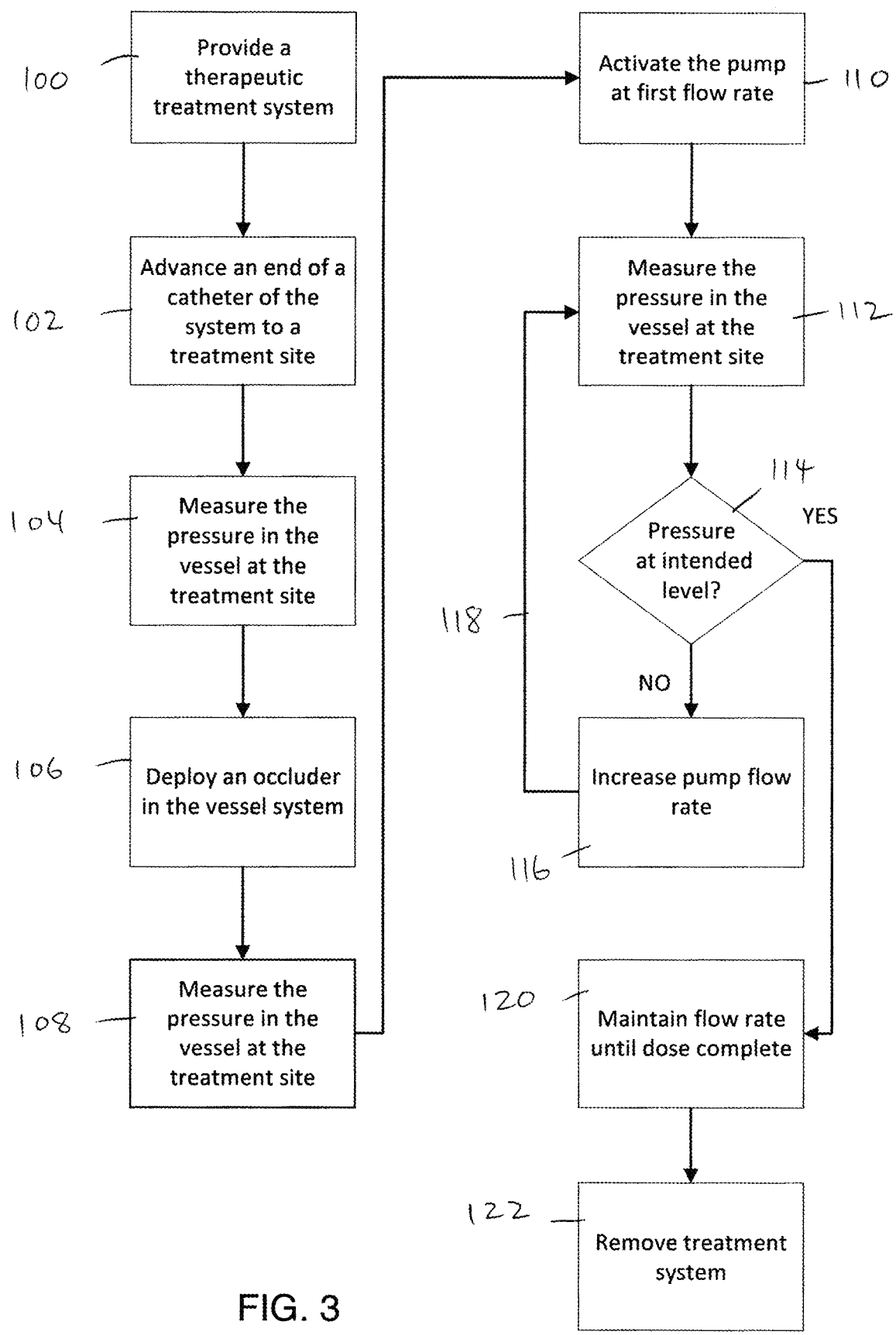
FIG. 3 is a flow chart of one method of therapeutic treatment through an artery to an organ.

With reference to the following description, the terms "proximal" and "distal" are defined in reference to the hand of a user of the devices and systems described herein, with the term "proximal" being closer to the user's hand, and the term "distal" being further from the user's hand such as to often be located further within a body of the patient during use.

Apparatus and methods are described herein related to the use of a system to inject a therapeutic agent into a primary vessel communicating with, for example, a tumor. For example, the tumor to be treated can be a solid tumor. In some cases, the tumor can be a cancerous tumor, such as a tumor specific to, by way of example only, cancer of the pancreas, kidney, liver, lung, or uterus.

As described herein, a treatment system is used to provide a therapeutic agent into a solid tumor by targeted infusion of the treatment into a region of tissue. The therapeutic agent is injected under relatively high pressure into a region of an organ or other defined area of tissue served by one or more feeder vessels.

Turning now to FIGS. 1 and 2, a therapeutic agent delivery system 10 is provided for the treatment of an organ with a vascular-infused therapeutic agent. In an embodiment, the delivery system 10 includes a catheter arrangement 12 having a vascular occluder 14, a pressure sensor system 16, and a pump system 18. The catheter 12 arrangement has a proximal end 20, a distal end 22, and a lumen 25 extending between its proximal and distal ends. The vascular occluder 14 is coupled to the distal end 22 of the catheter arrangement 12. The pressure sensor system 16 is provided to sense pressure at the distal end 22 of the catheter arrangement and/or within the lumen 25, and provides feedback to the pump system 18. The pump system 18 is adapted to control the rate of infusion of the therapeutic agent through the lumen 25 of the catheter arrangement based on the pressure sensed by the pressure sensor system 16.

The vascular occluder 14 is adapted to have a reduced diameter non-deployed configuration for intravascular advancement to a target location, and larger diameter deployed configuration once located at the target location. The deployment configuration can be either static or dynamic. A static occluder includes a fluid inflatable balloon, a self-expanding or manually expandable filter, and a mechanically expandable malecot catheter. These elements cause occlusion of the vessel by being sufficiently expanded to block flow within a vessel around a static occluder, and do not modulate in expansion in view of localized fluid pressure conditions within the vessel. A dynamic occluder is automatically and dynamically movable based on localized fluid pressure conditions about proximal and distal surfaces of the occluder. Such a dynamic occluder includes, by way of example, a microvalve that automatically expands to the diameter of the vessel in which it is deployed when subject to predetermined fluid pressure conditions and contracts to a smaller diameter away from the vessel wall when subject to relatively lower fluid pressure conditions. Dynamic microvalves are disclosed in detail in U.S. Pat. Nos. 8,696,698, 8,696,699, 9,539,081, 9,808,332, 9,770,319, 9,968,740, all assigned to Surefire Medical, Inc., which are all hereby incorporated by reference herein in their entireties. As disclosed in those patents, a dynamic microvalve can include a self-expanding filamentary braid having a frusto-conical portion with a low radial force of expansion and which is covered with a polymeric fabric. As an alternative, the filamentary braid with polymeric fabric may be dip-coated with a polymeric material to effectively increase with filamentary diameter and decrease the effective pore size of the microvalve. As yet another alternative, the filamentary braid may be directly dip-coated with a polymeric material (without first applying a fabric) to result in a non-porous polymeric membrane over the filamentary braid.

The catheter arrangement 12 is provided to configure the occluder 14 into a non-deployed configuration for delivery to a deployment location, deploy the occluder into the deployed configuration for injection of the therapeutic agent, and reconfigure the occluder back into the non-deployed configuration for removal from the patient after the therapy. Depending on the type of occluder, the catheter arrangement 12 can be a single catheter or may be a multiple catheter construct. For example, a single catheter can be used for a static balloon occluder or a single catheter dynamic microvalve device. (See previously incorporated U.S. Pat. No. 8,696,698). However, a preferred occluder, the dynamic microvalve described in previously incorporated U.S. Pat. No. 9,968,740, is deployed and reconfigured by longitudinal displacement of two catheters 12, 13 relative to each other. Thus, the catheter arrangement 12 can include an outer first catheter 12 and an inner second catheter 13 which are longitudinally displaceable relative to each other. The proximal end 46 of the microvalve 14 is attached to the distal end 22 of the first catheter 12, the distal end 48 of the microvalve 14 is attached to the distal end 23 of the second catheter 13, and the displacement of the two catheters reconfigures the occluder.

The catheter arrangement 12 includes at its proximal end a deployment handle 50. The handle 50 has a stationary portion 52 and a movable portion 54. The proximal end 20 of the outer first catheter 12 is longitudinally fixed relative to the stationary portion 52. The proximal end 21 of the inner second catheter 13 is coupled to the movable portion 54. In an embodiment, the movable portion 54 is a lockable slide. When the slide 54 is manually displaced relative to the stationary portion 52, the inner and outer catheters 12, 13 are longitudinally displaced relative to each other, and the occluder 14 is moved from one configuration to another and can be locked in such position using a lock 56. The handle 50 also includes a first fluid pathway 58 and a second fluid pathway 60. The first fluid pathway 58 extends to a first leur lock (or other connector) 62 and provides fluid communication between the pump system 18 and the lumen 25 of the catheter arrangement 12. The second fluid pathway 60 extends from a second leur lock (or other connector) 64 to a space (not shown) between the first and second inner and outer catheters 12, 13. The second fluid pathway 60 is preferably coupled to a source 66 of saline or other lubricous fluid that can be injected between the inner wall of outer catheter 12 and the outer wall of the inner catheter 13 to lubricate the surfaces thereof and facilitate relative movement between the two catheters 12, 13 when a force is applied at the slide 54.

The pressure sensor system 16 includes a pressure sensor 26 that is preferably in communication with the lumen 24 of the catheter, and preferably located at the distal end 22 of the catheter. Alternatively, the pressure sensor 26 may be located on the exterior of the catheter arrangement 12, distal of the largest diameter 14a of the occluder 14. Wires 28 extend through the wall of the catheter arrangement 12 from the sensor 26 to a housing 30 on the deployment handle 50. The housing 30 includes a control circuit (not shown), a display 34, and an actuation button 36. The display 34 visually indicates the pressure sensed at the pressure sensor 26. The display 34 may be an analog or a digital display. An analog display can include, e.g., a needle gauge or meter. A digital display may include a numerical readout or other suitable digital indicia using a screen, an arrangement of lights, or other indicia to indicate a sensed pressure. The pressure sensor 26 provides real-time feedback to the pump system 18.

The pump system 18 includes an infusion pump or injector (hereinafter, collectively 'pump') 40 adapted to infuse the therapeutic agent from a store 42 of agent through the lumen 24 of the catheter 12 at significantly more accurate and higher flow rates than manual injection permits. Such generated higher pressures allow resistance to therapeutic flow at the target tissue to be overcome, higher concentrations of therapeutic agent to be delivered to the target tissue, and higher residence time of therapeutic agent to be maintained in the target tissue to increase binding time of the therapeutic agent to the target tissue. The infusion pump 40 communicates with the pressure sensor system 16 and is adapted, based on feedback from the pressure sensor system 16, to automatically inject the therapeutic agent from the store 42 at higher (or, if necessary, lower) flow rates until a determined minimum pressure is reached or maintained during delivery of the dose of the therapeutic agent.

Using the system 10, models have been identified that permit delivery of the therapeutic agent to specific identified organs at respective delivery rates that generate significantly high pressures within the vessel and which result in overcoming the flow resistance, permit a desirable level of therapeutic agent concentration in the tissue, and provide an enhanced dwell time of the therapeutic agent in the tissue.

More importantly, the system 10 may be used in practice to provide the therapeutic agent to a localized region within a patient; i.e., a selected organ.

The therapeutic agent can include an immunotherapy agent, living cell therapies, chemoembolization agent, radio-embolization agent, contrast agent, lipiodol, chemotherapeutics, oncolytic viruses, gene therapies, cisplatin (or other alkylating agents), antibodies, checkpoint inhibitors, cytokines, oncolytic virus, cancer vaccines, cytotoxic agents, bland embolization agents, combination therapies, growth factor inhibitors, nanoparticle encapsulated therapies, and any other therapies that are fluid based, including pharmaceuticals, biologics and devices.

The organ can include the pancreas, the liver, the kidney, the lungs, the uterus, the ovaries, the cervix, the prostate, head and neck tissues (jaw, gums), the brain, the adrenal glands, bowel or colon, breast, thyroid, spleen, stomach, gall bladder, thymus, skin, bladder, lymph system, and various other organs or tissues subject to tumor or other disease states that can be treated with localized delivery of a therapeutic agent.

The diseases of the organs that can be treated are various. By way of example only, the following can be treated: adenocarcinomas including but not limited to metastatic tumors of the liver, colon, rectum, pancreas, ocular melanoma, breast cancer, triple negative breast cancer, primary cancers of the liver, pancreatic adenocarcinoma, melanoma, glioblastoma, bladder cancer, cervical cancer, ovarian cancer, gastric cancer, thyroid cancer, head and neck tumors; as well as sarcomas and any other solid tumors; diabetes; thyroid insufficiency; adrenal dysfunction, liver enzyme(s) dysfunction, thyroid dysfunction, general endocrine organ dysfunctions.

The necessary flow rate for a successful treatment is determined by the organ (vascularization, tissue density), disease state (tissue uniformity, disease progress), and the therapy (viscosity and Newtonian nature), such that general and valid statements about a preferred flow rate for each and every organ, disease state, and therapy may be difficult to construct. The feedback between the pressure sensor 16 and the pump 18 permit automatic targeting of an ideal flow rate for a successful treatment with a dose of therapeutic agent.

The system 10 may be used in either an arterial or a venous approach, preferably in a manner that most benefits delivery of the therapeutic agent under pressure to the particular target organ or other tissue. The system 10 and its use prevent, or at least minimize, systemic circulation of the therapeutic agent.

Turning now to FIG. 3, one method of using the system to treat an organ approached from an artery is described. Specifically, the treatment is directed to therapeutic delivery to the kidney. A treatment system 10 such as described above is provided at 100. The distal end of the catheter is advanced at 102 to the renal artery leading to the kidney. During such advancement, the occluder is configured in the non-deployed configuration in which it has a relatively small profile and is adapted to be tracked over a guidewire. Once the occluder reaches the deployment site and prior to its deployment, the pressure sensor is activated to measure at 104 the pressure in the vessel at the deployment site and display the measured pressure. The deployment handle is then actuated to deploy at 106 the occluder and the occluder expands in diameter. The post-deployment pressure in the vessel is sensed and displayed at 108. The post-deployment pressure in the vessel depends on the type of occluder.

TABLE 1

Therapeutic Pressures at Treated Organs

| Device | Arterial Animal/Organ | Segment | Pressure (mmHg) Baseline | Deployed | 0.4 mL/s | 0.8 mL/s | 1.2 mL/s |
|---|---|---|---|---|---|---|---|
| microcatheter | 976 Lt Kidney | Middle | 97 | 98 | 98 | 100 | 100 |
| balloon | 976 Lt Kidney | Lower pole | 98 | 19 | 58 | 58 | 71 |
| Surefire 025m microvalve | 976 Lt Kidney | Upper pole | 90 | 40 | 65 | 62 | 104 |
| microcatheter | 976 Rt Kidney | Middle | 98 | 98 | 98 | 97 | 96 |
| balloon | 976 Rt Kidney | Lower pole | 85 | 22 | 49 | 55 | 79 |
| Surefire 025m microvalve | 976 Rt Kidney | Upper pole | 93 | 40 | 53 | 80 | 103 |
| balloon | 977 Liver | Left Hepatic | 94 | 24 | 29 | 55 | 138 |
| Surefire 025m microvalve | 977 Liver | Rt Hepatic | 93 | 62 | 80 | 155 | 300 |

| Device | Venous Animal/Organ | Baseline | Pressure (mmHg) Deployed | 0.3 mL/m | 0.5 mL/m | 0.7 mL/m |
|---|---|---|---|---|---|---|
| Surefire 025m microvalve | 976 pancreas | 9 | 16 | 21 | 25 | 29 |
| Surefire 025m microvalve | 977 pancreas | 15 | 31 | 45 | 55 | 58 |

As shown in Table 1, when a standard microcatheter (with no occluder) is used to infuse therapeutic agent to the kidney (Left Kidney in Animal 976), the pressure in the vessel never significantly changes relative to a baseline pressure (mean arterial pressure) of 97-98 mmHg. This is because endogenous blood flow continues unimpeded. When a balloon occluder is used to infuse therapeutic agent to the kidney, the pressure in the vessel drops significantly (from 85-98 mmHg to 19-22 mmHg) as soon as the balloon is deployed. The occlusive design of the balloon blocks all antegrade blood flow in the vessel and the capillaries back fill the vessel to generate the sensed pressure. When the occluder is a microvalve such as the SUREFIRE 025m microvalve, available from Surefire Medical, Inc. of Westminster, CO, the change in intraarterial pressure is a drop, but much less significant (from 90-93 mmHg to 40 mmHg). This decrease in the magnitude of pressure change is a result of the construction and dynamic operation of the microvalve, which permits greater than 50%, more preferably greater than 65%, even more preferably greater than 75%, and even up to 90%, of the endogenous blood flow to continue past the microvalve-type occluder while the microvalve is in a deployed configuration. In fact, proprietary bench models that model pressure and flow rates and set the endogenous blood flow at 85% when the occluder is in a deployed configuration have been shown to be highly accurate relative to data recorded in vivo.

Then, after the pressure sensor senses the deployed pressure, the pump is actuated at 110 to deliver the therapeutic agent to the patient at a flow rate based on the sensed pressure. The flow rate of therapy, which was 0 mL/s prior to delivery, is incremented under control of the pump to a first flow rate, e.g., 0.4 mL/s. The pressure is again sensed at 112 during delivery at the first flow rate and fed back to the pump. If the pressure is not sufficiently high 114, the flow rate is adjusted up again at 116, and the pressure is sensed again, in a feedback loop 118. The process is repeated in the feedback loop 112 during dose delivery until a desirable pressure is reached at 120 that will result in deep tissue penetration. The desirable pressure is a threshold of a baseline pressure (i.e., the pressure when the occluder is in a pre-deployed configuration) plus some set incremental pressure. The baseline pressure for arterial side therapy is generally the mean arterial pressure, which generally resides between 90-100 mmHg. The incremental pressure may be 10 mmHg, or 20 mmHg, or 30 mmHg, or 40 mmHg, or some other pressure. After the organ is fully treated with a dose of the therapeutic agent, the deployment handle is operated to decrease the size of the occluder and the treatment system is removed from the patient at 122.

In distinction, using a standard microcatheter, the pressure does not change regardless of the flow rate. The opening in the catheter is too small and there is no barrier to prevent retrograde flow of the therapy. Using a balloon occluder, the pressure increases from 19 to 58 mmHg (0.4 mL/s), stays at 58 mmHg (0.8 mL/s) and increases to 70 mmHg (1.2 mL/s); however all such pressures remains below the endogenous pressure (98 mmHg) prior to deployment of the balloon. Therefore, the delivered therapeutic agent resides close to the balloon and has poor distal penetration. In distinction, using a microvalve occluder with this system, the pressure in the vessel rises based on the feedback. After deployment, the pressure increases from 40 to 65 mmHg (0.4 mL/s), stays around the same pressure at 62 mmHg (0.8 mL/s) and then significantly increases to 104 mmHg (1.2 mL/s). When the pressure increases to 104 mmHg, sufficient pressure is generated to cause the therapeutic agent to deeply penetrate the tissue as well as have increased residence time in the tissue.

Figure 4:
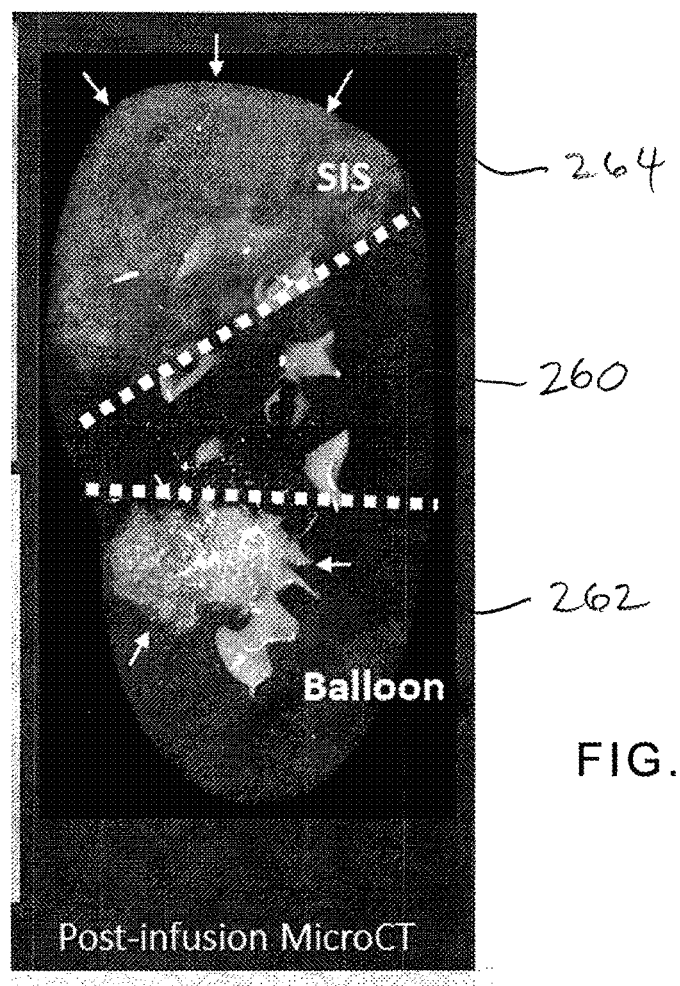
FIG. 4 is a fluoroscopic image of a contrast agent delivered to portions of the kidney with each of a microcatheter, a microcatheter with balloon occluder, and a microcatheter with microvalve occluder.

FIG. 4 shows the kidney of Animal 976 from the study of Table 1 perfusion of contrast agent lipiodol in place of a therapeutic agent to visually illustrate the depth of penetration of a therapeutic agent during use of each of the standard microcatheter (middle portion) 260, balloon occluder (lower portion) 262 and SUREFIRE microvalve (upper portion) 264. Note that the microcatheter provided very low penetration. The balloon occluder provided high density delivery close to the balloon, but did not provide delivery of the lipiodol deeper into the tissue. The SUREFIRE microvalve provided very deep penetration of tissues farthest from the catheter and the most uniform density of agent. Similar results were seen on studies of the right kidney of Animal 976, which is also presented in Table 1.

Another method of using the system for arterial side treatment is described with respect to therapeutic infusion to a liver, which is approached from the hepatic artery. In the hepatic artery prior to deployment, the mean arterial pressure is generally 93-94 mmHg. When the balloon occluder is deployed, the pressure in the vessel decreases significantly (down to 24 mmHg, all generated from capillary backfill, as discussed above).

However, when the occluder is a microvalve such as the SUREFIRE 025m microvalve, available from Surefire Medical, Inc. of Westminster, CO, the change in intraarterial pressure is much less significant (from 93-94 mmHg down to 62 mmHg). This difference in decrease in relation to the balloon, as discussed above, is a result of the construction and dynamic operation of the microvalve, which permits greater than 50%, more preferably greater than 65%, even more preferably greater than 75%, and even up to 90%, of the endogenous blood flow to continue past the microvalve-type occluder while the microvalve is in a deployed configuration. The effect is that a smaller amount of pressure has to be generated from the infused flow rate to overcome the pressure loss on deployment.

After the pressure sensor senses the deployed pressure, the pump is actuated to deliver the therapeutic agent to the patient at a flow rate based on the sensed pressure. The flow rate, which was 0 mL/s prior to delivery, is incremented under control of the pump, e.g., to 0.4 mL/s, and the pressure is sensed during the delivery and fed back to the pump. If the pressure is not sufficiently high, the flow is increased again, and the pressure is sensed again. The process is repeated during dose delivery until a desirable pressure is reached that will result in deep tissue penetration.

Figure 5:
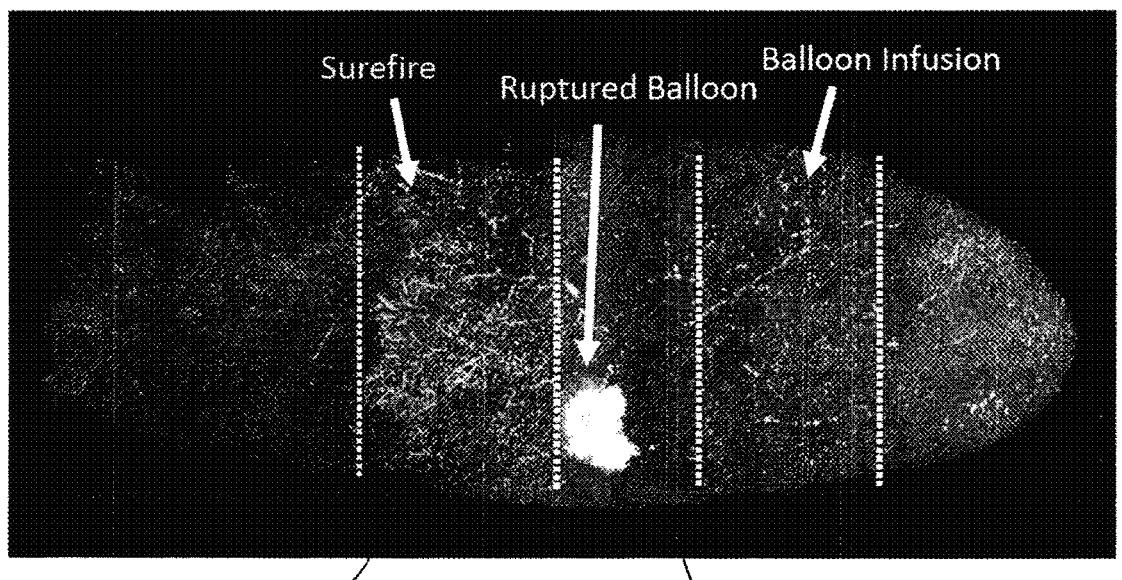
FIG. 5 is a fluoroscopic image of a contrast agent delivered to portions of the liver with each of a microcatheter with balloon occluder and a microcatheter with microvalve occluder.

Using a balloon occluder, the pressure increases from 24 mmHg (deployed) to 29 mmHg (0.4 mL/s), to 55 mmHg (0.8 mL/s), and then increases to 138 mmHg (1.2 mL/s). Thus, finally, at a flow rate of 1.2 mL/s, the balloon exceeds the baseline pressure of 93 mmHg. However, at such high pressures the balloon applies a very high radial force on the surrounding vessel wall which can lead to aneurysm and the balloon can be subject to rupturing, as shown at 302 in FIG. 5.

In distinction, using a dynamic microvalve occluder in the liver such that endogenous flow is permitted about the occluder and then builds upon that pressure, the pressure increases from 62 (deployed occluder) to 80 mmHg (0.4 mL/s), increases again to 165 mmHg (0.8 mL/s) and then significantly increases to 300 mmHg (1.2 mL/s). When the pressure increases to 165 mmHg and the even higher pressure of 300 mmHg is applied, such pressure causes the agent to deeply penetrate the tissue as well as have increased residence time in the tissue. Referring again to FIG. 5, here the SUREFIRE microvalve as part of the present system is shown to provide deep and uniform penetration of the liver tissue at 304. The microvalve is not an internally pressurized device and will not cause aneurysm because it applies a low radial force, and will not rupture even when subjected to these new high pressures. After the organ is fully treated with a full dose of the therapeutic agent, the deployment handle is operated to decrease the size of the occluder and the treatment system is removed from the patient.

A method of using the system to treat an organ approached from a vein is now described. Specifically the treatment is directed to therapeutic delivery to the tail of the pancreas; however, other organs can be treated via a venous route. A catheter with microvalve occluder is configured in the non-deployed configuration and tracked over a guidewire to a deployment site in the splenic vein. Prior to its deployment, the pressure sensor is activated to measure a baseline pressure in the vessel at the deployment site and display the baseline pressure. The deployment handle is then actuated to deploy the occluder and the occluder expands in diameter, and the post-deployment pressure in the vessel is sensed and displayed. The occluder is then deployed into a deployed configuration. For the dynamic microvalve occluder in a venous pathway, the deployed configuration blocks all of the endogenous flow in the vein and immediately generates a pressure exceeding the baseline. It should be recognized that such endogenous venous flow is opposite the endogenous arterial flow, and has a different effect on intravascular pressure when deployed. After deployment of the occluder, the pressure sensor is again utilized to measure the pressure in the vessel distal of the deployment site. The pressure immediately increases above baseline, as a pressure front is developed. Referring back to Table 1, treatment of the tail of the pancreas in Animal 976 shows that baseline pressure is 9 mmHg, and post-deployment pressure is 16 mmHg; and treatment of the tail of the pancreas in Animal 977 shows that baseline pressure is 15 mmHg, and post-deployment pressure is 31 mmHg.

The pump is then operated to inject the therapeutic agent through the lumen of the catheter and distal of the occluder at increasing flow rates (0.3 mL/min, 0.5 mL/min, and 0.7 mL/min) until the pressure sensor senses that a determined minimum pressure above the baseline pressure is reached. Note that venous infusion rates are conducted on the order of mL/minute (whereas arterial flow rates are conducted on the order of mL/second). In Animal 976, the pressure increased from 16 mmHg (at 0 mL/min) to 21 mmHg (at 0.3 mL/min) to 25 mmHg (at 0.5 mL/min) to 29 mmHg (at 0.7 mL/min). In Animal 977, the pressure increased from 31 mmHg (at 0 mL/min) to 45 mmHg (at 0.3 mL/min) to 55 mmHg (at 0.5 mL/min) to 58 mmHg (at 0.7 mL/min). On venous side therapy, the flow rate may be increased until the sensed pressure reaches a threshold of the baseline pressure (when the occluder is in a pre-deployed configuration) plus some set incremental pressure. The incremental pressure may be 5 mmHg, or 10 mmHg, or 20 mmHg, or 30 mmHg, or 40 mmHg, or some other pressure. The flow rate of therapeutic agent from the pump is then maintained or modulated to keep the pressure in the vessel elevated to at least the minimum pressure above baseline for the duration of the dose delivery. After the dose of the therapeutic agent has been delivered, the occluder is collapsed and the system is removed from the patient.

The lymphatic system can also be treated in a manner similar to treatment through the vessels described above. Lymphatic vasculature resides within the same target organs and can be accessed using cannula or catheter. In these cases, therapeutics can be delivered under pressure to perfuse target tissue in a manner similar to that of the arterial or venous system. It some cases, local regional infusion though the lymphatic system may be advantageous as tumor metastases invade the lymphatic system and can travel to other regions of the body. The lymphatic system is a low pressure system and can be treated similarly to treatment via a vein.

In any of vessel, the flow resistance can be calculated as pressure generated in the vessel divided by the fluid flow rate within the vessel. The flow rate is generated by any endogenous flow in addition to therapy infused by the pump. The pressure generated upon such flow can be directly and instantly measured by the sensor. Thus, the resistance to flow is calculated by dividing the measured pressure by the fluid flow rate. This provides an instantaneous resistance, which may or may not necessarily be accurate at all times. Therefore it may be desirable to normalize the measured resistance. To do so, multiple flow resistances can be calculated and then averaged.

Based on the (normalized) flow resistance, the therapeutic agent can be infused at a flow rate into the tumor such that the minimum pressure is exceeded. In various embodiments, the minimum pressure may be exceeded by a pressure of at least 0 mmHg, and more preferably a pressure in excess of the minimum pressure that is within a range of pressures (upper and lower limits) that is specific to the tumorous organ being treated. The infusion flow rate is increased at least until a measured pressure corresponding to the intravascular pressure at the site of therapeutic delivery is within the range of pressures determined to be suitable for a tumor type, specific organ, and/or therapy. Once such flow rate is reached, the flow rate may remain constant or may be varied, preferably remaining within the range of pressures, and such that the minimum pressure is exceeded during remaining delivery of the therapeutic agent. Infusion of the therapeutic agent via the automated pump delivers higher and more consist flow rates than achievable via a manual injection device, such as a syringe. Such infusion process permits improved efficacy, consistency and reliability for patient treatment relative to prior treatments.

In another method of delivering a therapeutic agent under enhanced pressure, the minimum pressure to overcome a flow resistance through a type of tumor or disease state in each of various organs is predetermined and stored in a database of such values. The therapeutic agent is infused at a flow rate into the tumor such that the minimum pressure is exceeded. In various embodiments, the minimum pressure may be exceeded by a pressure exceeding at least 0 mmHg relative to a baseline minimum pressure, and more preferably a pressure within a range of pressures that is specific to the tumorous organ being treated. The infusion flow rate is increased at least until a measured pressure corresponding to the intravascular pressure at the site of therapeutic delivery is within a range of pressures determined to be suitable for a tumor type, specific organ, and/or therapy. Once such flow rate is reached, the flow rate may remain constant or may be varied, preferably within the range, and such that the minimum pressure is exceeded during remaining delivery of the therapeutic agent. Such infusion process permits improved efficacy, consistency and reliability for patient treatment.

In a method of delivering a therapeutic agent to a tumor of a patient, several steps were carried out. First, a physical benchtop model was developed for simulated infusion into a tumor suffering interstitial fluid pressure on a target vessel. Second, the model was correlated to anatomical data. Third, the model was used to predict perfusion characteristics of the tumor, e.g., tumor physiology and flow resistance, based on sensed pressure at the target vessel under various infusion rates. Fourth, based on the perfusion characteristics, a therapeutic treatment plan is identified. Fifth, based on the treatment plan, one or more therapeutic agents is infused into the patient systemically or locally to treat the tumor. Optionally and sixth, after the delivery of one or more therapeutic agents in accord with at least an initial step of the treatment plan and the pressures sensed during one or more flow rates of agent delivery during the treatment, the treatment plan may be modified. Steps five and six may be repeated until the entire dose of treatment is delivered. Now, more specifically, the steps of the method are further described.

Figure 6:
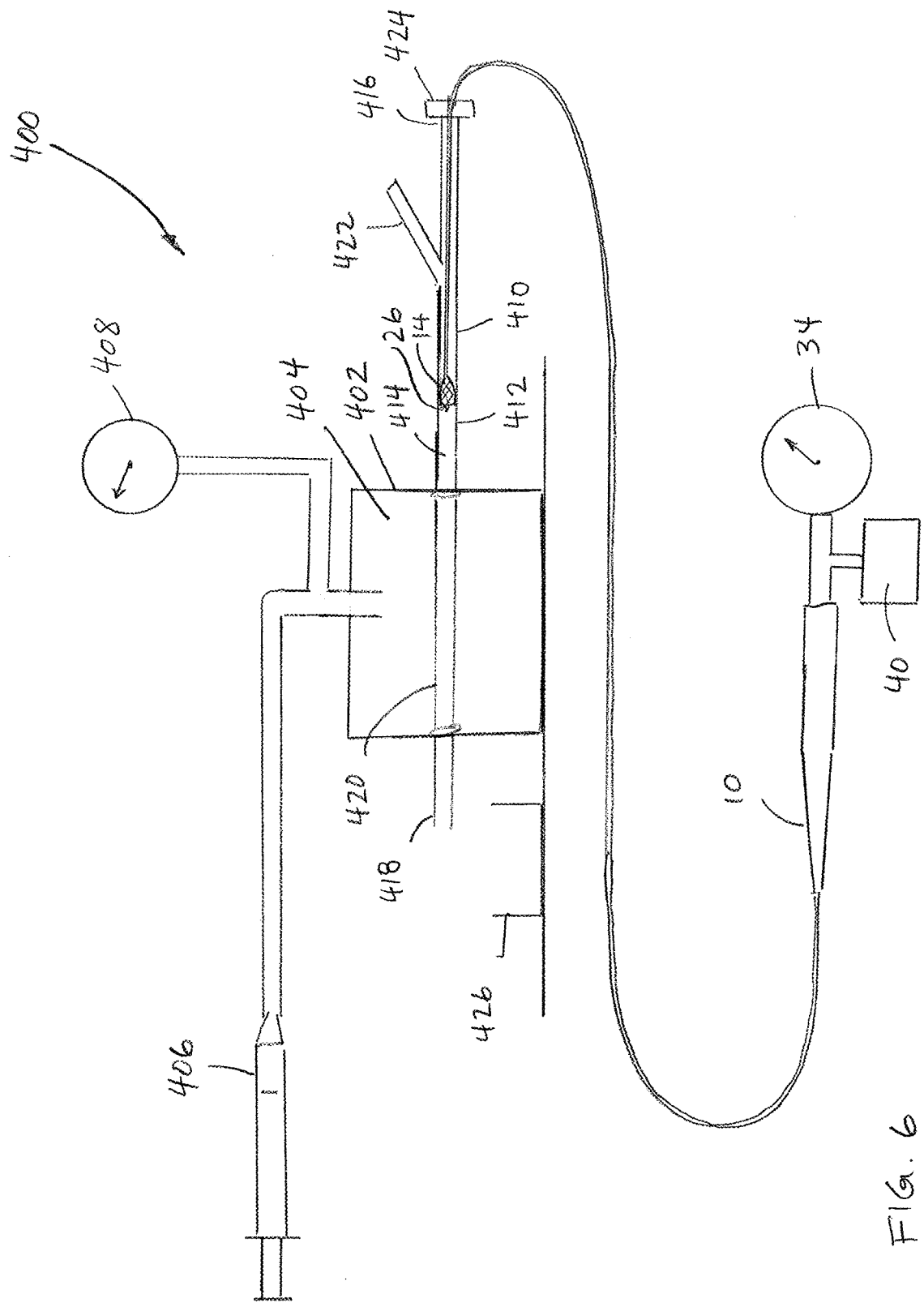
FIG. 6 is a schematic diagram of a modelling system for modelling interstitial fluid pressure in a tumor.

Referring now to FIG. 6, a benchtop model 400 was constructed to model interstitial fluid pressure in a tumor, a compliant target vessel extending through the tumor and subject to the interstitial fluid pressure, and a low pressure shunting vessel. The model 400 included a closed pressurizable chamber 402 having an interior 404, a pressure applicator 406 to pressurize the interior of the chamber, and a pressure sensor 408 for sensing a pressure at the interior of the chamber. Tubing 410 was provided having a wall 412 defining a lumen 414 with an opening 416, an exit 418 and a central portion 420. The wall 412 at at least the central portion 420 was compliant such that the central portion was resiliently deformable to alter the size of the lumen 414 therein when an exterior of the wall 412 was subject to a pressure greater than a pressure at the interior of the lumen, i.e., by pressurizing the interior 404 of the chamber relative to the lumen 414. The central portion 420 was extended within the interior 404 of the chamber 402. A shunting line 422 was extended from the tubing 410 at a location between the opening 416 and the interior 404 of the chamber 402, with the shunting line 422 open to atmospheric pressure. In the constructed model, the pressure applicator 406 was a manually operable syringe fluidly coupled to the chamber to provide pressurized air into the chamber. Other pressure applicators, including powered pumps and injectors can alternatively be used. In the constructed model, the pressure sensor 408 was a mechanical gauge that sensed within the chamber and displayed the sensed pressure; electronic sensors and displays can alternatively be used. In the constructed model, the central portion 420 of the tubing extended diametrically through the chamber 402. In the constructed model, the shunting line 422 was a Y-shaped branch off the tubing and open to atmosphere. In the constructed model, a valved port 424 was provided at the opening 416 of the lumen 414 for receiving an infusion device, and the exit 418 of the lumen was provided on an opposite side of the chamber 402. The exit 418 leads to a fluid collection vessel 426.

A dynamic microvalve occluder infusion device 10 of the type previously described having a pressure sensor 26 at its distal occluder 14 was provided and advanced through the port 424, beyond the shunting line 422 and into the central portion 420 of compliant tubing 410 located within the chamber 402. The device 10 was coupled to a injector 40 adapted to infuse fluid at various selected flow rates and, as previously described, is coupled to a display 34 to indicate pressure sensed at pressure sensor 26.

The interior 404 of the chamber 402 was then pressurized at a specified pressure, and a series of 10 ml infusions of saline were made through the microvalve occluder 10 at specific infusion rates. A first pressure may be atmospheric pressure or a higher pressure. The liquid that passed through the central portion 420 of tubing within the chamber 402 and out of the exit 418 was collected in vessel 426 and weighed to determine a percentage of infused fluid delivered through the central portion 420. The chamber pressure was then increased, and the infusion, fluid collection, and determination of percentage of fluid delivery was repeated. The pressure within the chamber was adjusted to each of several different pressures, and the process repeated for each pressure. As the interior 404 of the chamber 402 increased in pressure relative to the lumen interior, the tubing 410 collapsed in diameter, resulting in increased resistance to fluid flow.

Based on the collected data, the measured pressure sensed at the microvalve occluder was correlated to flow resistance through the central portion 420 of the tubing 410 as it collapsed under pressure. This correlated data modelled a tumor microenvironment in which interstitial fluid pressure restricts blood flow through pinched vasculature. As tumor pressure increases, the pressure detected at the microvalve occluder at any given infusion rate likewise predictably increases. Further, the microvalve occluder is able to overcome the resistance of the tumor, thereby delivering significantly more therapeutic agent to the target region than an infusion device lacking a dynamic microvalve.

In an embodiment, a device is tracked to a region of interest associated with a tumor burden in a vessel of a vascular system within a test subject (either human or animal) or a patient. A microvalve occluder device, balloon, or other vascular occluder device is then deployed in the vessel. A contrast agent is infused into the region of interest at different infusion rates, titrating from low rates (low pressure) to high rates (high pressure). The vascular pressure is monitored, and fluoroscopic imaging is performed at each infusion step. The imaging identifies a coverage of contrast (percent enhancement) and magnitude of enhancement (intensity of enhancing pixels in the image) which are correlated with a pressure sensed in the vessel at the tumor to determine a physiology of the tumor. The percent enhancement determines the volume of tissue accessible in a given flow and pressure condition. The magnitude of enhancement provides information of the vascularity of the tissue and the volume of therapeutic agent that can be delivered in the enhancing vessels. By monitoring of the vascular pressure during infusion, information is obtained regarding the anatomy and interstitial tissue pressure of the tumor.

Based on this knowledge, prior to or at the time of treatment, the tumor physiology is analyzed using both an imaging technique and sensed pressure within the tumor. According to a preferred method of imaging, a dynamic microvalve occluder is advanced to a target vessel in communication with the tumor, a contrast agent is infused at a predetermined flow rate into the vessel, and an image is made of the contrast-enhanced region. In addition, while the contrast agent is infused, the pressure that develops within the target vessel is measured. Based on the flow rate of the contrast agent, the extent of imaged contrast-enhancement, and the sensed pressure, the tumor physiology is diagnosed; i.e., it is determined whether the tumor is enhanced with contrast at low flow rates, the extent of such contrast enhancement through the tumor, and whether such contrast enhancement increases as the flow rate and resulting pressure increases.

In a first example, upon infusion of the contrast agent at low flow rates and under low pressure, imaging of the tumor shows that the tumor is highly enhanced. No new regions of enhancement are identified at higher flows rates and higher pressures. Computationally, the percent of enhancing volume within the tumor remains static even as the infusion rate of the contrast agent increases, and the enhancement intensity increases uniformly through the tumor tissue as infusion rate increases. Calculations are performed based on the volume of the tumor that is enhanced (as the contrast will only be present in the blood vessels) to determine tumor vascularity. Further, the sensed pressure increases as infusion rate increases while the slope of the increase is shallow. From the above, the tumor can be diagnosed as hypervascular and well perfused. Cells within the tumor are expected to be aerobic and rapidly dividing. Systemic chemotherapy is likely to penetrate the tumor body. Example suitable systemic chemotherapies include gemcitabine, oxaliplatin, cisplatin, doxorubicin, 5-fluorouracil (5-FU), topotecan, irinotecan, folinic acid, and etoposide. local-regional therapy may be administered using standard flow directed devices to increase concentration of the therapeutic agent reaching the tumor. Reflux protection devices can be used to prevent non-target delivery.

In a second example, infusion of contrast agent at low flow rates results in enhancement of regions of the tumor under imaging. As flow rate of contrast agent increases, imaging indicates a greater volume of tissue enhancement. Computationally, it is determined that a percent enhancing volume increases as infusion rate increases. Enhancement intensity increases heterogeneously, with low pressure high flow regions displaying significantly higher intensity than high pressure low flow regions. In an embodiment, calculations are performed based on enhancing volume of tumor (as the contrast will only be present in the blood vessels) to determine tumor vascularity in the different regions of the tumor. In addition, the pressure sensor records an increased pressure in the vessel as the infusion rate increases. The slope of the pressure increase is steeper than expected for a low pressure tumor. Discontinuities in slope are identified, and appear as increased pressure opens pinched vessels, changing the addressable volume of tumor. Stabilization of pressure slope indicates all addressable volume of tissue has been accessed. Pressure and imaging data can be interpolated to determine the percentage of tissue accessible at different pressures and flow rates. This provides information on the percentage of tissue that is expected to respond to a given therapy. The magnitude of pressure needed to access tissue will provide information on the likely aerobic proliferative or anaerobic quiescent nature of the tumor cells. Calculations based on pressure versus flow measurements are performed to calculate the percentage of tumor volume with open vascularity and the volume having increasing degrees of resistance. From the above, the tumor can be diagnosed as heterogeneous, with regions of both high perfusion, low pressure tissue and low perfusion, high pressure tissue. Systemic chemotherapy may be used to reduce a portion of the tumor burden. A percentage of the tissue is expected to respond to therapies targeted to proliferative cells such as gemcitabine, oxaliplatin, cisplatin, doxorubicin, 5-fluorouracil (5-FU), topotecan, irinotecan, folinic acid, and etoposide. In addition, local-regional therapy should be conducted using a microvalve occluder. Infusion rate criteria should be selected based on the slope stabilization point determined in the pressure mapping procedure. A combination of therapeutics can be delivered to treat aerobic and anerobic tissues. Proliferative tissues can be treated using standard chemotherapies as listed for systemic infusion. Anerobic quiescent tissue may be treated using metabolic disrupters that disrupt glycolysis such as phloretin, 2-Deoxyglucose, 3-Bromopyruvate, lonidamine, FX11 (Lactate Dehydrogenase A Inhibitor), Oxamate, Dichloroacetate, WZB117, C75 (inhibitor of fatty acid synthase), Silybin, and phenformin. Alternatively or in conjunction, tumor cell specific immunotherapy or viral therapy agents may be utilized.

In a third example, imaging indicates that the tumor minimally enhances at low flow rates of contrast agent; however, as the flow rate of the contrast agent increases, more tissue volume enhances. Computationally, percent enhancing volume increases as the infusion rate increases. Enhancement intensity increases heterogeneously, with lower pressure higher flow regions displaying significantly higher intensity than very high pressure very low flow regions. Calculations are performed based on enhancing the volume of tumor (as the contrast will only be present in the blood vessels) to determine tumor vascularity in the different regions of the tumor. The pressure sensed in the vessel increases as the infusion rate of the contrast agent increases. The slope of the increase is steeper than in well or moderately well perfused tumors. Discontinuities in slope may be apparent as increased pressure opens pinched vessels, changing the addressable volume of tumor. Stabilization of pressure slope indicates all addressable volume of tissue has been accessed. From the above, the tumor is diagnosed as one which high pressure, low flow tissue that is unlikely to respond to traditional systemic chemo or loco-regional flow directed therapies. Treatment is determined to benefit from loco-regional infusion of therapy at high pressure using a microvalve occluder or balloon. Administration pressure/flow requirements of the therapy are determined based on the diagnostic run. A combination of therapeutics can be delivered to treat aerobic and anerobic tissues. Proliferative tissues can be treated using standard chemotherapies as listed for systemic infusion. Anerobic quiescent tissue may be treated using metabolic disrupters that disrupt glycolysis such as phloretin, 2-Deoxyglucose, 3-Bromopyruvate, lonidamine, FX11 (Lactate Dehydrogenase A Inhibitor), Oxamate, Dichloroacetate, WZB117, C75 (inhibitor of fatty acid synthase), Silybin, and phenformin. Alternatively or in conjunction, tumor cell specific immunotherapy or viral therapy agents may be utilized. Calculations based on pressure versus flow measurements are preferably performed to calculate a percentage of tumor volume accessible with different flow and pressure situations.

It should be understood that the diagnostic and treatment methods can be applied to a range of chemotherapeutics, biologicals, or other therapeutic agents. It should also be understood that knowledge of the tumor physiology can help select specific agents with known physiological response. For example, if the tumor is displaying hypervascular tissue characteristics, a vascular endothelial growth factor (VEGF) inhibitor may be effective at controlling tumor growth and promoting ingress of treatment into the tumor mass. If the tumor is hypovascular, an extracellular matrix disrupter, such as recombinant human hyaluronidase (by way of example, Hylenex® marketed by Halozyme Therapeutics, Inc., San Diego, CA), may be employed in a local regional high-pressure infusion to break up the tumor structure and make it more susceptible to other types of therapeutics.

In addition, to tailoring the therapy flow rate to meet minimum pressure levels, the therapy can also be optimized by total infusion time and total dose of therapy delivered. Such parameters can be optimized based on underlying disease characteristics of the tumor of the organ, such as tumor size, tumor type, or information gained from medical imaging of the tumor such as CT, CT angiography, PET, MR, diffusion weighted MR or other modality that can characterize the relative perfusion flow and pressure in a target tumor. Particularly with venous-side infusion, where a minimal applied pressure above baseline results in flooding of the organ with the therapy, it may be desirable to maintain low flow rates above baseline for a determined period of time to infuse a dose of therapy. Longer duration of therapy results in longer dwell time of the therapy in the tumor, where it can be effective.

From the above, an embodiment of the system can be characterized as a catheter having a proximal end, a distal end, and a lumen extending between the proximal and distal ends; an occluder provided at the distal end of the catheter, the occluder having a non-deployed configuration and a deployed configuration, the occluder having an expanded diameter in the deployed configuration that extends across the vessel; a pressure sensor system configured to sense a pressure on a distal side of the occluder; and a pump communicating with the pressure sensor, the pump adapted to inject the therapeutic agent at multiple flow rates, and wherein the pump is configured to adjust the flow rate of the therapeutic agent through the lumen of catheter based on the pressure sensed by the pressure sensor. The occluder is preferably a dynamic microvalve that dynamically opens and closes to change size in the vessel based on a pressure gradient between the proximal and distal sides of the microvalve; i.e., when there is relatively higher pressure at the proximal side the valve permits antegrade flow past the valve, and when there is relatively higher pressure at the distal side the valve opens to the vessel wall to prevent retrograde flow there past.

Further, the system can be used to deliver a therapeutic agent into a vessel by advancing the distal end of the catheter through a vessel to a target location, wherein during the advancing, the occluder is in the non-deployed configuration; deploying the occluder; then sensing a pressure corresponding to a pressure in the vessel with the pressure sensor;

infusing the therapeutic agent through the lumen of catheter at a flow rate based on the sensed pressure; and repeating the sensing and infusing until the sensed pressure reaches a minimum threshold pressure. The method is ideal for therapeutic agent delivery to an organ through a venous approach.

In addition, the system can be tailored to a specific organ. In such case, the organ to which the therapeutic agent is to be delivered is identified; a minimum pressure at which the therapeutic agent is to be delivered to the organ is determined; the distal end of the catheter is delivered through the vessel adjacent the organ, wherein during the advancing the occluder is in the non-deployed configuration; the occluder is deployed; and then the pressure distal of the occluder is sensed with the pressure sensor. The therapeutic agent is delivered through a lumen of catheter at an incremental flow rate based on the sensed pressure, and the sensing and agent delivery is repeated until the sensed pressure reaches at least the determined minimum pressure. In a preferred embodiment, the therapeutic agent is infused at a maintained flow rate that results in maintaining or exceeding the determined minimum pressure for a duration of a delivery of a dose of the therapeutic treatment. Thus, a sensed pressure is used to determine a condition for optimum delivery of treatment, rather than an end point of treatment.

Moreover, the therapeutic agent is preferably delivered at a flow rate that generates a fluid pressure in the vessel such that a flow resistance to the therapeutic agent is overcome. The flow resistance is calculated as the fluid pressure generated in the vessel divided by the total fluid flow rate within the vessel, the total fluid flow rate is the sum of therapy flow rate and endogenous flow rate, and the fluid pressure generated by total fluid flow rate is measured adjacent a locus of delivery of the therapeutic agent in the vessel.

There have been described and illustrated herein embodiments of systems and methods for intravascular delivery of a therapeutic agent to an organ. While particular embodiments of the invention have been described, it is not intended that the invention be limited thereto, as it is intended that the invention be as broad in scope as the art will allow and that the specification be read likewise. Thus, it is recognized that the systems and methods may be applied to both humans and animals. Also, while examples of organs, disease states, and therapeutic agents have been provided, such lists are not meant to be exclusive and the systems and methods are intended to be used where ever they would have therapeutic utility, in association with any such organs, disease states, and therapeutic agents. Also, while several single and double catheter arrangements are described, any catheter arrangement using one or more catheters and wherein the at least one catheter has one or more lumen is intended within the meaning of "catheter arrangement." Further, while several types of static and dynamic occluders have been described, other static and dynamic occluders may be used as well to assemble the systems and accomplish the methods described herein. It will therefore be appreciated by those skilled in the art that yet other modifications could be made to the provided invention without deviating from its scope as claimed.

We claim:

1. A system for delivery of a therapeutic agent into a vessel having a vessel wall, comprising:
 a) a catheter arrangement including an outer catheter having a proximal end and a distal end, and an inner catheter having a proximal end and a distal end and extending through and longitudinally displaceable relative to the outer catheter, the inner catheter having a lumen extending between the proximal end of the inner catheter and the distal end of the inner catheter and opening at an axial distal orifice at the distal end of the inner catheter;
 b) a deployment handle having a stationary portion and a movable portion, the proximal end of the outer catheter longitudinally fixed relative to the stationary portion, and the proximal end of the inner catheter coupled to the movable portion, the deployment handle including a lock to lock a relative position of the movable portion relative to the stationary portion and consequently a position of the inner catheter relative to the outer catheter;
 c) an occluder fixed to both the distal end of the inner catheter and the distal end of the outer catheter and proximal of the axial distal orifice of the inner catheter, the occluder having a non-deployed configuration caused by the inner catheter and the outer catheter being in a first longitudinal position relative to each other and a deployed configuration caused by the inner catheter and the outer catheter being longitudinally displaced relative to the first longitudinal position, the occluder having an expanded diameter in the deployed configuration relative to a diameter in the non-deployed configuration, such that when in the deployed configuration the occluder extends,
 the occluder is dynamic such that, when in the deployed configuration, the occluder automatically moves to change size in response to surrounding fluid pressure conditions such that when higher fluid pressure is exerted on a proximal side of the occluder than at a distal side of the occluder, the occluder decreases in size to permit flow past the occluder, and when higher pressure is exerted at the distal side of the occluder than at the proximal side of the occluder, the occluder expands into contact with the vessel wall;
 d) a pressure sensor configured to sense a fluid pressure in the vessel on the distal side of the occluder; and
 e) a pump communicating with the pressure sensor, the pump adapted to infuse the therapeutic agent through the lumen of the inner catheter and out of the axial distal orifice at multiple flow rates, and wherein the pump is configured to adjust a flow rate of the therapeutic agent through the lumen of the inner catheter based on the fluid pressure sensed by the pressure sensor.

2. The system of claim 1, wherein the occluder comprises a braid of filaments.

3. The system of claim 2, wherein the braid of the occluder is covered in a fabric.

4. The system of claim 3, wherein the fabric is a polymer.

5. The system of claim 2, wherein the braid of the occluder is covered in a polymeric membrane.

6. The system of claim 1, wherein the occluder is a microvalve.

7. A method of delivering a dose of a therapeutic agent through a vein to an organ, comprising:
 a) providing the system according to claim 1;
 b) advancing a distal end of the catheter arrangement through the vein to a target location in fluid communication with the organ, wherein during the advancing, the occluder is in the non-deployed configuration;
 c) deploying the occluder; then
 d) sensing the fluid pressure corresponding to a pressure in the vein with the pressure sensor;

e) infusing the therapeutic agent through the lumen of the inner catheter with the pump at the flow rate based on the fluid pressure sensed by the pressure sensor;

f) repeating steps d) and e) until the fluid pressure sensed by the pressure sensor reaches a minimum threshold pressure; and then g) maintaining the infusion of the therapeutic agent at at least the flow rate necessary to maintain or exceed the minimum threshold pressure for a duration of delivery of the dose of the therapeutic agent.

8. The method according to claim 7, further comprising sensing the fluid pressure with the pressure sensor prior to deploying the occluder.

9. A method of delivering a therapeutic agent through a vein of a patient, comprising:

a) providing the system according to claim 1;

b) advancing a distal end of the catheter arrangement with the occluder in the non-deployed configuration to the vein;

c) deploying the occluder into the deployed configuration within the vein; and then d) infusing the therapeutic agent with the pump at a therapy flow rate that generates the fluid pressure in the vein such that a flow resistance to the therapeutic agent is overcome, wherein, the flow resistance is calculated as the fluid pressure generated in the vein divided by a total fluid flow rate within the vein, the total fluid flow rate is a sum of the therapy flow rate and an endogenous flow rate, and the fluid pressure generated by the total fluid flow rate is measured by the pressure sensor adjacent a locus of delivery of the therapeutic agent in the vein.

10. The method of claim 9, wherein when the occluder is deployed, the occluder is dynamically movable based on localized fluid pressure conditions within the vein.

11. A method of delivering a therapeutic agent into a vessel, comprising:

a) providing the system according to claim 1;

b) advancing a distal end of the catheter arrangement through the vessel to a target location, wherein during the advancing, the occluder is in the non-deployed configuration;

c) deploying the occluder into the deployed configuration; then d) sensing the fluid pressure in the vessel with the pressure sensor;

e) infusing the therapeutic agent with the pump through the lumen of the inner catheter at the flow rate based on the fluid pressure sensed by the pressure sensor; and f) repeating steps d) and e) until the fluid pressure sensed by the pressure sensor reaches a minimum threshold pressure.

12. The method of claim 11, further comprising sensing the fluid pressure with the pressure sensor prior to deploying the occluder.

13. The method of claim 11, wherein the vessel is an artery.

14. The method of claim 11, wherein the vessel is a vein.

15. The method of claim 11, wherein the vessel is a lymphatic vessel.

16. A method of delivering a therapeutic agent into a vessel directly communicating with an organ, comprising:

a) providing the system according to claim 1;

b) identifying the organ to which the therapeutic agent is to be delivered;

c) determining a minimum pressure at which the therapeutic agent is to be delivered to the organ;

d) advancing a distal end of the catheter arrangement through the vessel, wherein during the advancing the occluder is in the non-deployed configuration;

e) deploying the occluder into the deployed configuration; then f) sensing the fluid pressure in the vessel distal of the occluder with the pressure sensor;

g) infusing the therapeutic agent through the lumen of the inner catheter with the pump at an incremental flow rate based on the fluid pressure sensed by the pressure sensor; and h) repeating steps f) and g) until the fluid pressure sensed by the pressure sensor reaches at least the determined minimum pressure.

17. The method of claim 16, further comprising:

maintaining the infusion of the therapeutic agent at at least the flow rate necessary to maintain or exceed the determined minimum pressure for a duration of a delivery of a dose of the therapeutic agent.

18. The method of claim 16, wherein:

the determining is from a stored database of values.

19. The method of claim 16, wherein:

after the sensing, displaying the fluid pressure sensed by the pressure sensor on a display.

20. The method of claim 19, wherein:

the displaying is localized to a proximal end of the catheter arrangement.

21. The method of claim 16, wherein the vessel is an artery.

22. The method of claim 16, wherein the vessel is a vein.

23. The method of claim 16, wherein the vessel is a lymphatic vessel.

24. A method of delivering a therapeutic agent into a vessel, the vessel having a total fluid flow rate therein that generates a pressure, comprising:

a) providing the system according to claim 1;

b) advancing a distal end of the catheter arrangement through the vessel to a target location, wherein during the advancing, the occluder is in the non-deployed configuration;

c) deploying the occluder into the deployed configuration; then d) sensing the fluid pressure in the vessel with the pressure sensor;

e) infusing the therapeutic agent through the lumen of the inner catheter with the pump at the flow rate based on the fluid pressure sensed by the pressure sensor; and f) repeating steps d) and e) until the fluid pressure sensed by the pressure sensor reaches a minimum threshold pressure.

25. The method of claim 24, further comprising:

maintaining the infusion of the therapeutic agent at at least the flow rate necessary to maintain or exceed the minimum threshold pressure for a duration of a delivery of a dose of the therapeutic agent.

26. The method of claim 24, wherein the vessel is an artery.

27. The method of claim 24, wherein the vessel is a vein.

28. The method of claim 24, wherein the vessel is a lymphatic vessel.

29. A method of delivering a therapeutic agent through a vessel of a patient, comprising:
   a) providing the system according to claim 1;
   b) advancing a distal end of the catheter arrangement with the occluder in the non-deployed configuration to the vessel;
   c) deploying the occluder into the deployed configuration; and then
   d) delivering the therapeutic agent with the pump at a therapy flow rate that generates the fluid pressure in the vessel such that a flow resistance to the therapeutic agent is overcome, wherein,
   the flow resistance is calculated as the fluid pressure generated in the vessel divided by a total fluid flow rate within the vessel,
   the total fluid flow rate is a sum of the therapy flow rate and an endogenous flow rate, and
   the fluid pressure generated by the total fluid flow rate is measured by the pressure sensor adjacent a locus of delivery of the therapeutic agent in the vessel.

30. The method of claim 29, wherein the endogenous flow rate exceeds 0 mL/s.

31. The method of claim 29, wherein the vessel is an artery and the endogenous flow rate when the occluder is deployed is between 0-10% of the endogenous flow rate when the occluder is non-deployed.

32. The method of claim 29, wherein the vessel is an artery and the endogenous flow rate when the occluder is deployed is greater than 50% of the endogenous flow rate when the occluder is non-deployed.

33. The method of claim 29, wherein the vessel is an artery and the endogenous flow rate when the occluder is deployed is greater than 65% of the endogenous flow rate when the occluder is non-deployed.

34. The method of claim 29, wherein the vessel is an artery and the endogenous flow rate when the occluder is deployed is greater than 80% of the endogenous flow rate when the occluder is non-deployed.

35. The method of claim 29, wherein the vessel is a vein and the endogenous flow rate when the occluder is deployed is between 0-10% of the endogenous flow rate when the occluder is non-deployed.

36. The method of claim 29, wherein the occluder when deployed is dynamically movable based on localized fluid pressure conditions within the vessel.

\* \* \* \* \*